(12) United States Patent
Khalil et al.

(10) Patent No.: US 9,956,409 B2
(45) Date of Patent: *May 1, 2018

(54) SPINAL CORD STIMULATOR SYSTEM

(71) Applicant: GLOBUS MEDICAL, INC., Audubon, PA (US)

(72) Inventors: Saif Khalil, Wayne, PA (US); Raghavendra Angara, Norristown, PA (US); Miles Curtis, Philadelphia, PA (US); Christopher Biele, King of Prussia, PA (US); Daniel Fellmeth, Eagleville, PA (US)

(73) Assignee: Globus Medical, Inc., Audubon, PA (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/453,024

(22) Filed: Mar. 8, 2017

(65) Prior Publication Data
US 2017/0173336 A1  Jun. 22, 2017

Related U.S. Application Data

(63) Continuation of application No. 15/058,682, filed on Mar. 2, 2016, now Pat. No. 9,623,246, which is a (Continued)

(51) Int. Cl.
*A61N 1/00* (2006.01)
*A61N 1/36* (2006.01)
(Continued)

(52) U.S. Cl.
CPC ......... *A61N 1/36071* (2013.01); *A61N 1/025* (2013.01); *A61N 1/0551* (2013.01);
(Continued)

(58) Field of Classification Search
CPC .................................................. A61N 1/36021
(Continued)

(56) References Cited

U.S. PATENT DOCUMENTS 3,195,540 A  7/1965 Waller
3,718,134 A  2/1973 Brindley
(Continued)

*Primary Examiner* — Nadia A Mahmood

(57) ABSTRACT

Spinal cord stimulation (SCS) system having a recharging system with self alignment, a system for mapping current fields using a completely wireless system, multiple independent electrode stimulation outsource, and control through software on Smartphone/mobile device and tablet hardware during trial and permanent implants. SCS system can include multiple electrodes, multiple, independently programmable, stimulation channels within an implantable pulse generator (IPG) providing concurrent, but unique stimulation fields. SCS system can include a replenishable power source, rechargeable using transcutaneous power transmissions between antenna coil pairs. An external charger unit, having its own rechargeable battery, can charge the IPG replenishable power source. A real-time clock can provide an auto-run schedule for daily stimulation. A bi-directional telemetry link informs the patient or clinician the status of the system, including the state of charge of the IPG battery. Other processing circuitry in current IPG allows electrode impedance measurements to be made.

20 Claims, 11 Drawing Sheets

Related U.S. Application Data continuation of application No. 14/667,730, filed on Mar. 25, 2015, now Pat. No. 9,302,108, which is a continuation of application No. 14/173,510, filed on Feb. 5, 2014, now Pat. No. 9,440,076.

(60) Provisional application No. 61/792,654, filed on Mar. 15, 2013.

(51) Int. Cl.
*A61N 1/02* (2006.01)
*A61N 1/05* (2006.01)
*A61N 1/372* (2006.01)
*A61N 1/375* (2006.01)
*A61N 1/378* (2006.01)

(52) U.S. Cl.
CPC ....... *A61N 1/0553* (2013.01); *A61N 1/36125* (2013.01); *A61N 1/36157* (2013.01); *A61N 1/36178* (2013.01); *A61N 1/36185* (2013.01); *A61N 1/3754* (2013.01); *A61N 1/3787* (2013.01); *A61N 1/37217* (2013.01); *A61N 1/37229* (2013.01); *A61N 1/37241* (2013.01)

(58) Field of Classification Search
USPC ...................................................... 607/2, 46
See application file for complete search history.

(56) References Cited

U.S. PATENT DOCUMENTS

| | | |
|---|---|---|
| 3,724,467 A | 4/1973 | Avery et al. |
| 3,727,616 A | 4/1973 | Lenzkes |
| 3,822,708 A | 7/1974 | Zilber |
| 3,867,950 A | 2/1975 | Fischell |
| 3,888,260 A | 6/1975 | Fischell |
| 3,942,535 A | 3/1976 | Schulman |
| 4,014,346 A | 3/1977 | Brownlee et al. |
| 4,019,518 A | 4/1977 | Maurer et al. |
| 4,082,097 A | 4/1978 | Mann et al. |
| 4,134,408 A | 1/1979 | Brownlee et al. |
| 4,232,679 A | 11/1980 | Schulman |
| 4,379,462 A | 4/1983 | Borkan et al. |
| 4,390,023 A | 6/1983 | Rise |
| 4,408,608 A | 10/1983 | Daly et al. |
| 4,459,989 A | 7/1984 | Borkan |
| 4,510,936 A | 4/1985 | Fourcin et al. |
| 4,512,351 A | 4/1985 | Pohndorf |
| 4,541,432 A | 9/1985 | Molina-Negro et al. |
| 4,549,556 A | 10/1985 | Tarjan et al. |
| 4,608,986 A | 9/1986 | Beranek et al. |
| 4,640,286 A | 2/1987 | Thomson |
| 4,690,145 A | 9/1987 | King-Smith et al. |
| 4,712,558 A | 12/1987 | Kidd et al. |
| 5,036,850 A | 8/1991 | Owens |
| 5,119,832 A | 6/1992 | Xavier |
| 5,143,067 A | 9/1992 | Rise et al. |
| 5,255,691 A | 10/1993 | Otten |
| 5,279,292 A | 1/1994 | Baumann et al. |
| 5,314,457 A | 5/1994 | Jeutter et al. |
| 5,354,320 A | 10/1994 | Schaldach et al. |
| 5,374,285 A | 12/1994 | Vaiani et al. |
| 5,391,193 A | 2/1995 | Thompson |
| 5,411,537 A | 5/1995 | Munshi et al. |
| 5,417,719 A | 5/1995 | Hull et al. |
| 5,441,527 A | 8/1995 | Erickson et al. |
| 5,443,486 A | 8/1995 | Hrdlicka et al. |
| 5,458,629 A | 10/1995 | Baudino et al. |
| 5,458,631 A | 10/1995 | Xavier |
| 5,501,703 A | 3/1996 | Holsheimer et al. |
| 5,591,217 A | 1/1997 | Barreras |
| 5,630,835 A | 5/1997 | Brownlee |
| 5,643,330 A | 7/1997 | Holsheimer et al. |
| 5,662,689 A | 9/1997 | Elsberry et al. |
| 5,690,693 A | 11/1997 | Wang et al. |
| 5,702,431 A | 12/1997 | Wang et al. |
| 5,713,939 A | 2/1998 | Nedungadi et al. |
| 5,733,313 A | 3/1998 | Barreras et al. |
| 5,733,322 A | 3/1998 | Starkebaum |
| 5,769,877 A | 6/1998 | Barreras, Sr. |
| 5,843,146 A | 12/1998 | Cross, Jr. |
| 5,861,019 A | 1/1999 | Sun et al. |
| 5,865,843 A | 2/1999 | Baudino |
| 5,893,383 A | 4/1999 | Torgerson et al. |
| 5,895,416 A | 4/1999 | Barreras et al. |
| 5,913,882 A | 6/1999 | King |
| 5,935,159 A | 8/1999 | Cross, Jr. et al. |
| 5,938,690 A | 8/1999 | Law et al. |
| 6,009,350 A | 12/1999 | Renken |
| 6,052,623 A | 4/2000 | Fenner et al. |
| 6,052,624 A | 4/2000 | Mann |
| 6,120,502 A | 9/2000 | Michelson |
| 6,167,312 A | 12/2000 | Goedeke |
| 6,169,925 B1 | 1/2001 | Villaseca et al. |
| 6,175,769 B1 | 1/2001 | Errico et al. |
| 6,181,969 B1 | 1/2001 | Gord |
| 6,181,971 B1 | 1/2001 | Doan |
| 6,185,452 B1 | 2/2001 | Schulman et al. |
| 6,185,463 B1 | 2/2001 | Baudino |
| 6,205,361 B1 | 3/2001 | Kuzma et al. |
| 6,208,894 B1 | 3/2001 | Schulman et al. |
| 6,216,045 B1 | 4/2001 | Black et al. |
| 6,227,204 B1 | 5/2001 | Baumann et al. |
| 6,236,892 B1 | 5/2001 | Feler |
| 6,240,317 B1 | 5/2001 | Villaseca et al. |
| 6,240,318 B1 | 5/2001 | Phillips |
| 6,249,705 B1 | 6/2001 | Snell |
| 6,249,707 B1 | 6/2001 | Kohnen et al. |
| 6,266,564 B1 | 7/2001 | Hill et al. |
| 6,309,401 B1 | 10/2001 | Redko et al. |
| 6,379,300 B1 | 4/2002 | Haubrich |
| 6,381,496 B1 | 4/2002 | Meadows et al. |
| 6,393,325 B1 | 5/2002 | Mann et al. |
| 6,415,187 B1 | 7/2002 | Kuzma et al. |
| 6,456,256 B1 | 9/2002 | Amundson et al. |
| 6,456,887 B1 | 9/2002 | Dudding et al. |
| 6,463,329 B1 | 10/2002 | Goedeke |
| 6,473,653 B1 | 10/2002 | Schallhorn et al. |
| 6,477,424 B1 | 11/2002 | Thompson et al. |
| 6,505,072 B1 | 1/2003 | Linder et al. |
| 6,505,401 B1 | 1/2003 | Doan |
| 6,516,227 B1 | 2/2003 | Meadows et al. |
| 6,522,932 B1 | 2/2003 | Kuzma et al. |
| 6,535,766 B1 | 3/2003 | Thompson et al. |
| 6,539,253 B2 | 3/2003 | Thompson et al. |
| 6,553,263 B1 | 4/2003 | Meadows et al. |
| 6,553,264 B2 | 4/2003 | Redko et al. |
| 6,587,724 B2 | 7/2003 | Mann |
| 6,600,954 B2 | 7/2003 | Cohen et al. |
| 6,609,031 B1 | 8/2003 | Law et al. |
| 6,609,032 B1 | 8/2003 | Woods et al. |
| 6,614,406 B2 | 9/2003 | Amundson et al. |
| 6,622,048 B1 | 9/2003 | Mann et al. |
| 6,650,944 B2 | 11/2003 | Goedeke et al. |
| 6,654,642 B2 | 11/2003 | Boydston et al. |
| 6,658,297 B2 | 12/2003 | Loeb |
| 6,658,302 B1 | 12/2003 | Kuzma et al. |
| 6,662,052 B1 | 12/2003 | Sarwal et al. |
| 6,662,053 B2 | 12/2003 | Borkan |
| 6,664,763 B2 | 12/2003 | Echarri et al. |
| 6,671,544 B2 | 12/2003 | Baudino |
| 6,675,045 B2 | 1/2004 | Mass et al. |
| 6,675,046 B2 | 1/2004 | Holsheimer |
| 6,708,065 B2 | 3/2004 | Von Arx et al. |
| 6,741,892 B1 | 5/2004 | Meadows et al. |
| 6,745,079 B2 | 6/2004 | King |
| 6,757,970 B1 | 7/2004 | Kuzma et al. |
| 6,795,737 B2 | 9/2004 | Gielen et al. |
| 6,809,701 B2 | 10/2004 | Amundson et al. |
| 6,819,958 B2 | 11/2004 | Weiner et al. |
| 6,847,849 B2 | 1/2005 | Mamo et al. |
| 6,850,802 B2 | 2/2005 | Holsheimer |
| 6,868,288 B2 | 3/2005 | Thompson |

(56) References Cited

U.S. PATENT DOCUMENTS

| | | |
|---|---|---|
| 6,871,099 B1 | 3/2005 | Whitehurst et al. |
| 6,889,086 B2 | 5/2005 | Mass et al. |
| 6,892,097 B2 | 5/2005 | Holsheimer |
| 6,895,280 B2 | 5/2005 | Meadows et al. |
| 6,895,283 B2 | 5/2005 | Erickson et al. |
| 6,901,292 B2 | 5/2005 | Hrdlicka et al. |
| 6,909,917 B2 | 6/2005 | Woods et al. |
| 6,920,359 B2 | 7/2005 | Meadows et al. |
| 6,930,602 B2 | 8/2005 | Dublin et al. |
| 6,937,891 B2 | 8/2005 | Leinders et al. |
| 6,941,171 B2 | 9/2005 | Mann et al. |
| 6,950,706 B2 | 9/2005 | Rodriguez et al. |
| 6,950,709 B2 | 9/2005 | Baudino |
| 6,981,314 B2 | 1/2006 | Black et al. |
| 6,985,088 B2 | 1/2006 | Goetz et al. |
| 6,993,384 B2 | 1/2006 | Bradley |
| 7,009,313 B1 | 3/2006 | Parramon et al. |
| 7,016,733 B2 | 3/2006 | Dublin et al. |
| 7,023,359 B2 | 4/2006 | Goetz et al. |
| 7,024,246 B2 | 4/2006 | Acosta et al. |
| 7,035,690 B2 | 4/2006 | Goetz |
| 7,039,470 B1 | 5/2006 | Wessman |
| 7,047,076 B1 | 5/2006 | Li et al. |
| 7,047,081 B2 | 5/2006 | Kuzma |
| 7,047,082 B1 | 5/2006 | Schrom et al. |
| 7,047,627 B2 | 5/2006 | Black et al. |
| 7,051,419 B2 | 5/2006 | Schrom et al. |
| 7,076,304 B2 | 7/2006 | Thompson |
| 7,099,718 B1 | 8/2006 | Thacker et al. |
| 7,107,102 B2 | 9/2006 | Daignault, Jr. et al. |
| 7,110,824 B2 | 9/2006 | Amundson et al. |
| 7,127,296 B2 | 10/2006 | Bradley |
| 7,127,297 B2 | 10/2006 | Law et al. |
| 7,127,298 B1 | 10/2006 | He et al. |
| 7,142,909 B2 | 11/2006 | Greenberg et al. |
| 7,146,223 B1 | 12/2006 | King |
| 7,162,306 B2 | 1/2007 | Caby et al. |
| 7,174,215 B2 | 2/2007 | Bradley |
| 7,177,690 B2 | 2/2007 | Woods et al. |
| 7,177,691 B2 | 2/2007 | Meadows et al. |
| 7,177,702 B2 | 2/2007 | Wallace et al. |
| 7,181,286 B2 | 2/2007 | Sieracki et al. |
| 7,184,836 B1 | 2/2007 | Meadows et al. |
| 7,187,978 B2 | 3/2007 | Malek et al. |
| 7,206,642 B2 | 4/2007 | Pardo et al. |
| 7,211,103 B2 | 5/2007 | Greenberg et al. |
| 7,212,133 B2 | 5/2007 | Goetz et al. |
| 7,215,991 B2 | 5/2007 | Besson et al. |
| 7,225,032 B2 | 5/2007 | Schmeling et al. |
| 7,239,918 B2 | 7/2007 | Strother et al. |
| 7,239,920 B1 | 7/2007 | Thacker et al. |
| 7,248,929 B2 | 7/2007 | Meadows et al. |
| 7,254,443 B2 | 8/2007 | Jelen et al. |
| 7,254,445 B2 | 8/2007 | Law et al. |
| 7,254,446 B1 | 8/2007 | Erckson et al. |
| 7,263,406 B2 | 8/2007 | Toy et al. |
| 7,295,876 B1 | 11/2007 | Erickson |
| 7,295,878 B1 | 11/2007 | Meadows et al. |
| 7,310,873 B2 | 12/2007 | Pardo et al. |
| 7,317,948 B1 | 1/2008 | King et al. |
| 7,324,852 B2 | 1/2008 | Barolat et al. |
| 7,337,003 B2 | 2/2008 | Malinowski |
| 7,359,751 B1 | 4/2008 | Erickson et al. |
| 7,359,755 B2 | 4/2008 | Jones et al. |
| 7,363,079 B1 | 4/2008 | Thacker et al. |
| 7,369,897 B2 | 5/2008 | Boveja et al. |
| 7,376,466 B2 | 5/2008 | He et al. |
| 7,389,146 B2 | 6/2008 | Hanson et al. |
| 7,389,147 B2 | 6/2008 | Wahlstrand et al. |
| 7,428,438 B2 | 9/2008 | Parramon et al. |
| 7,437,193 B2 | 10/2008 | Parramon et al. |
| 7,437,197 B2 | 10/2008 | Harris et al. |
| 7,444,181 B2 | 10/2008 | Shi et al. |
| 7,444,184 B2 | 10/2008 | Boveja et al. |
| 7,463,927 B1 | 12/2008 | Chaouat |
| 7,471,986 B2 | 12/2008 | Hatlestad |
| 7,483,752 B2 | 1/2009 | Von Arx et al. |
| 7,489,966 B2 | 2/2009 | Leinders et al. |
| 7,496,404 B2 | 2/2009 | Meadows et al. |
| 7,499,755 B2 | 3/2009 | Cross, Jr. |
| 7,515,968 B2 | 4/2009 | Metzler et al. |
| 7,519,432 B2 | 4/2009 | Bolea et al. |
| 7,526,341 B2 | 4/2009 | Goetz et al. |
| 7,539,538 B2 | 5/2009 | Parramon et al. |
| 7,546,164 B2 | 6/2009 | King |
| 7,548,788 B2 | 6/2009 | Chinn et al. |
| 7,551,963 B2 | 6/2009 | Rusin et al. |
| 7,555,346 B1 | 6/2009 | Woods et al. |
| 7,571,001 B2 | 8/2009 | Thacker et al. |
| 7,580,753 B2 | 8/2009 | Kim et al. |
| 7,603,179 B1 | 10/2009 | Grandhe |
| 7,613,518 B2 | 11/2009 | Qin et al. |
| 7,617,006 B2 | 11/2009 | Metzler et al. |
| 7,630,749 B2 | 12/2009 | Squeri |
| 7,647,121 B2 | 1/2010 | Wahlstrand et al. |
| 7,650,192 B2 | 1/2010 | Wahlstrand |
| 7,657,319 B2 | 2/2010 | Goetz et al. |
| 7,658,196 B2 | 2/2010 | Ferreri et al. |
| 7,672,734 B2 | 3/2010 | Anderson et al. |
| 7,684,869 B2 | 3/2010 | Bradley et al. |
| 7,684,873 B2 | 3/2010 | Gerber |
| 7,697,995 B2 | 4/2010 | Cross, Jr. et al. |
| 7,706,888 B2 | 4/2010 | Jolly |
| 7,715,912 B2 | 5/2010 | Rezai et al. |
| 7,715,924 B2 | 5/2010 | Rezai et al. |
| 7,725,196 B2 | 5/2010 | Machado et al. |
| 7,729,781 B2 | 6/2010 | Swoyer et al. |
| 7,734,340 B2 | 6/2010 | De Ridder |
| 7,734,342 B2 | 6/2010 | Gielen et al. |
| 7,738,963 B2 | 6/2010 | Hickman et al. |
| 7,738,966 B2 | 6/2010 | Skubitz et al. |
| 7,742,810 B2 | 6/2010 | Moffitt et al. |
| 7,742,821 B1 | 6/2010 | Vamos et al. |
| 7,747,330 B2 | 6/2010 | Nolan et al. |
| 7,761,167 B2 | 7/2010 | Bennett et al. |
| 7,761,170 B2 | 7/2010 | Kaplan et al. |
| 7,761,985 B2 | 7/2010 | Hegland et al. |
| 7,765,005 B2 | 7/2010 | Stevenson |
| 7,765,011 B2 | 7/2010 | Skubitz et al. |
| 7,769,462 B2 | 8/2010 | Meadows et al. |
| 7,787,960 B2 | 8/2010 | Lubenow et al. |
| 7,797,048 B2 | 9/2010 | Stevenson et al. |
| 7,797,054 B2 | 9/2010 | Skubitz et al. |
| 7,797,057 B2 | 9/2010 | Harris |
| 7,801,600 B1 | 9/2010 | Carbunaru et al. |
| 7,801,602 B2 | 9/2010 | McClure et al. |
| 7,801,615 B2 | 9/2010 | Meadows et al. |
| 7,801,621 B1 | 9/2010 | Thacker et al. |
| 7,803,021 B1 | 9/2010 | Brase |
| 7,805,189 B2 | 9/2010 | Stein et al. |
| 7,805,197 B2 | 9/2010 | Bradley |
| 7,813,796 B2 | 10/2010 | Greenberg et al. |
| 7,813,803 B2 | 10/2010 | Heruth et al. |
| 7,813,809 B2 | 10/2010 | Strother et al. |
| 7,818,068 B2 | 10/2010 | Meadows et al. |
| 7,831,306 B2 | 11/2010 | Finch et al. |
| 7,831,311 B2 | 11/2010 | Cross, Jr. et al. |
| 7,831,313 B2 | 11/2010 | Lauro |
| 7,835,795 B2 | 11/2010 | Alexander et al. |
| 7,844,343 B2 | 11/2010 | Wahlstrand et al. |
| 7,848,817 B2 | 12/2010 | Janzig et al. |
| 7,848,818 B2 | 12/2010 | Barolat et al. |
| 7,848,819 B2 | 12/2010 | Goetz et al. |
| 7,848,820 B2 | 12/2010 | Abrahamson |
| 7,853,330 B2 | 12/2010 | Bradley et al. |
| 7,856,277 B1 | 12/2010 | Thacker et al. |
| 7,860,568 B2 | 12/2010 | Deininger et al. |
| 7,860,570 B2 | 12/2010 | Whitehurst et al. |
| 7,872,884 B2 | 1/2011 | Parramon et al. |
| 7,881,796 B2 | 2/2011 | Scott et al. |
| 7,881,805 B2 | 2/2011 | Bradley et al. |
| 7,885,712 B2 | 2/2011 | Goetz et al. |
| 7,891,085 B1 | 2/2011 | Kuzma et al. |
| 7,899,542 B2 | 3/2011 | Cowan et al. |

(56) References Cited

U.S. PATENT DOCUMENTS

| | | |
|---|---|---|
| 7,904,148 B2 | 3/2011 | Greenberg et al. |
| 7,908,013 B2 | 3/2011 | Miesel et al. |
| 7,930,030 B2 | 4/2011 | Woods et al. |
| 7,930,037 B2 | 4/2011 | Heruth et al. |
| 7,930,039 B2 | 4/2011 | Olson |
| 7,933,656 B2 | 4/2011 | Sieracki et al. |
| 7,937,158 B2 | 5/2011 | Erickson et al. |
| 7,941,227 B2 | 5/2011 | Barker |
| 7,949,393 B2 | 5/2011 | Varrichio et al. |
| 7,957,797 B2 | 6/2011 | Bourget et al. |
| 7,957,809 B2 | 6/2011 | Bourget et al. |
| 7,957,814 B2 | 6/2011 | Goetz et al. |
| 7,970,003 B2 | 6/2011 | Holt |
| 7,974,703 B2 | 7/2011 | Goetz et al. |
| 7,974,705 B2 | 7/2011 | Zdeblick et al. |
| 7,979,126 B2 | 7/2011 | Payne et al. |
| 7,979,131 B2 | 7/2011 | Feler et al. |
| 7,979,133 B2 | 7/2011 | Feler et al. |
| 7,983,757 B2 | 7/2011 | Miyazawa et al. |
| 7,983,762 B2 | 7/2011 | Gliner et al. |
| 7,983,766 B1 | 7/2011 | Thacker et al. |
| 7,987,000 B2 | 7/2011 | Moffitt et al. |
| 7,991,482 B2 | 8/2011 | Bradley |
| 7,996,091 B2 | 8/2011 | Harris |
| 8,000,794 B2 | 8/2011 | Lozano |
| 8,000,800 B2 | 8/2011 | Takeda et al. |
| 8,005,547 B2 | 8/2011 | Forsberg et al. |
| RE42,682 E | 9/2011 | Barreras et al. |
| 8,019,427 B2 | 9/2011 | Moffitt |
| 8,019,438 B2 | 9/2011 | Johnson et al. |
| 8,019,439 B2 | 9/2011 | Kuzma et al. |
| 8,019,440 B2 | 9/2011 | Kokones et al. |
| 8,019,443 B2 | 9/2011 | Schleicher et al. |
| 8,032,224 B2 | 10/2011 | Miesel et al. |
| 8,036,737 B2 | 10/2011 | Goetz et al. |
| 8,036,747 B2 | 10/2011 | Thacker et al. |
| 8,036,754 B2 | 10/2011 | Lee et al. |
| 8,044,635 B2 | 10/2011 | Peterson |
| 8,046,073 B1 | 10/2011 | Pianca |
| 8,050,769 B2 | 11/2011 | Gharib et al. |
| 8,055,337 B2 | 11/2011 | Moffitt et al. |
| 8,065,013 B2 | 11/2011 | Bradley et al. |
| 8,073,542 B2 | 12/2011 | Doerr |
| 8,082,034 B2 | 12/2011 | Keacher |
| 8,082,039 B2 | 12/2011 | Kim et al. |
| 8,086,317 B2 | 12/2011 | Finch et al. |
| 8,086,318 B2 | 12/2011 | Strother et al. |
| 8,108,048 B2 | 1/2012 | Masoud |
| 8,108,049 B2 | 1/2012 | King |
| 8,108,051 B2 | 1/2012 | Cross, Jr. et al. |
| 8,108,052 B2 | 1/2012 | Boling |
| 8,116,880 B2 | 2/2012 | Cross, Jr. |
| 8,121,697 B2 | 2/2012 | Greenberg et al. |
| 8,121,701 B2 | 2/2012 | Woods et al. |
| 8,121,702 B2 | 2/2012 | King |
| 8,126,567 B2 | 2/2012 | Gerber et al. |
| 8,131,358 B2 | 3/2012 | Moffitt et al. |
| 8,135,477 B2 | 3/2012 | Fattouh et al. |
| 8,140,168 B2 | 3/2012 | Olson et al. |
| 8,150,530 B2 | 4/2012 | Wesselink |
| 8,150,533 B2 | 4/2012 | Wessman |
| 8,155,750 B2 | 4/2012 | Jaax et al. |
| 8,155,752 B2 | 4/2012 | Aghassian et al. |
| 8,165,678 B2 | 4/2012 | Forsberg et al. |
| 8,170,674 B2 | 5/2012 | Pyles et al. |
| 8,170,675 B2 | 5/2012 | Alatarls et al. |
| 8,175,719 B2 | 5/2012 | Shi et al. |
| 8,175,720 B2 | 5/2012 | Skelton et al. |
| 8,180,445 B1 | 5/2012 | Moffitt |
| 8,180,451 B2 | 5/2012 | Hickman et al. |
| 8,180,462 B2 | 5/2012 | Inman et al. |
| 8,185,207 B2 | 5/2012 | Molnar et al. |
| 8,185,212 B2 | 5/2012 | Carbunaru et al. |
| 8,195,297 B2 | 6/2012 | Penner |
| 8,195,304 B2 | 6/2012 | Strother et al. |
| 8,204,595 B2 | 6/2012 | Pianca et al. |
| 8,209,014 B2 | 6/2012 | Doerr |
| 8,209,021 B2 | 6/2012 | Alataris et al. |
| 8,214,051 B2 | 7/2012 | Sieracki et al. |
| 8,214,057 B2 | 7/2012 | Barolat |
| 8,224,453 B2 | 7/2012 | De Ridder |
| 8,260,425 B2 | 9/2012 | Kokones et al. |
| 8,285,388 B2 | 10/2012 | Wahlstrand |
| 2003/0191504 A1 | 10/2003 | Meadows et al. |
| 2005/0107841 A1 | 5/2005 | Meadows et al. |
| 2006/0235484 A1 | 10/2006 | Jaax et al. |
| 2008/0051839 A1 | 2/2008 | Libbus et al. |
| 2009/0024187 A1 | 1/2009 | Erickson et al. |
| 2009/0030487 A1 | 1/2009 | Lang |
| 2009/0270935 A1 | 10/2009 | Zhao et al. |
| 2009/0326608 A1 | 12/2009 | Huynh et al. |
| 2011/0184486 A1 | 7/2011 | De Ridder |
| 2013/0079600 A1 | 3/2013 | Engmark et al. |
| 2013/0096651 A1 | 4/2013 | Ozawa et al. |
| 2014/0067007 A1 | 3/2014 | Drees et al. |
| 2014/0277264 A1 | 9/2014 | Khalil et al. |
| 2014/0314170 A1 | 10/2014 | Plumb et al. |

SPINAL CORD STIMULATOR SYSTEM

CROSS REFERENCE TO RELATED APPLICATIONS

This application is a continuation of U.S. patent application Ser. No. 15/058,682 filed on Mar. 2, 2016 (published as U.S. Patent Publication No. 2016-0250471), which is a continuation application of U.S. patent application Ser. No. 14/667,730 filed on Mar. 25, 2015 (issued as U.S. Pat. No. 9,302,108), which is a continuation application of U.S. patent application Ser. No. 14/173,510 filed on Feb. 5, 2014 (now issued as U.S. Pat. No. 9,440,076) which is a non-provisional patent application that claims priority to provisional application No. 61/792,654 filed on Mar. 15, 2013, all of which are incorporated by reference in their entirety herein.

TECHNICAL FIELD

This disclosure relates to stimulators using electrical pulses in a medical context, and more particularly, applying electrical pulse stimulators to the spinal cord to control pain.

BACKGROUND

A Spinal Cord Stimulator (SCS) is used to exert pulsed electrical signals to the spinal cord to control chronic pain. Spinal cord stimulation, in its simplest form, comprises stimulating electrodes implanted in the epidural space, an electrical pulse generator implanted in the lower abdominal area or gluteal region, conducting wires connecting the electrodes to the electrical pulse generator, an electrical pulse generator remote control, and an electrical pulse generator charger. Spinal cord stimulation has notable analgesic properties and, at the present, is used mostly in the treatment of failed back surgery syndrome, complex regional pain syndrome and refractory pain due to ischemia.

Electrotherapy of pain by neurostimulation began shortly after Melzack and Wall proposed the gate control theory in 1965. This theory proposed that nerves carrying painful peripheral stimuli and nerves carrying touch and vibratory sensation both terminate in the dorsal horn (the gate) of the spinal cord. It was hypothesized that input to the dorsal horn of the spinal cord could be manipulated to "close the gate" to the nerves. As an application of the gate control theory, Shealy et al. implanted the first spinal cord stimulator device directly on the dorsal column for the treatment of chronic pain in 1971.

Spinal cord stimulation does not eliminate pain. The electrical impulses from the stimulator override the pain messages so that the patient does not feel the pain intensely. In essence, the stimulator masks the pain. A trial implantation is performed before implanting the permanent stimulator. The physician first implants a trial stimulator through the skin (percutaneously) perform stimulations as a trial run. Because a percutaneous trial stimulator tends to move from its original location, it is considered temporary. If the trial is successful, the physician can then implant a permanent stimulator. The permanent stimulator is implanted under the skin of the abdomen, with the leads inserted under the skin and subcutaneously fed to and inserted into the spinal canal. This placement of the stimulator in the abdomen is a more stable, effective location. The leads, which consist of an array of electrodes, can be percutaneous type or paddle type. Percutaneous electrodes are easier to insert in comparison with paddle type, which are inserted via incision over spinal cord and laminectomy.

There are a number of the problems that exist in currently available SCS systems that limit the full benefits of dorsal column stimulation from an effectiveness and patient user friendly perspective. One problem is that current SCS systems are limited to only 16 electrodes with a maximum of 16 independent current sources. Another problem is that current SCS systems have complicated trialing methods that involve multiple gadgets and hardware. Another problem is that patients must carry an independent remote control in order to control the IPG in their daily lives.

SUMMARY

Disclosed are the following features included within a spinal cord stimulation system: (1) a recharging system with self-alignment, (2) a system for mapping current fields using a completely wireless system, (3) multiple independent electrode stimulation outsource, and (4) IPG control, during trial and permanent implants, through software on generic Smartphone/mobile device and tablet hardware. The SCS system can include multiple electrodes, and multiple, independently programmable, stimulation channels within an implantable pulse generator (IPG) where the channels can provide concurrent, but unique stimulation fields, permitting virtual electrodes to be realized. The SCS system can include a replenishable power source (e.g., rechargeable battery) that may be recharged using transcutaneous power transmissions between antenna coil pairs. An external charger unit, having a rechargeable battery can be used to charge the IPG replenishable power source. A real-time clock can provide an auto-run schedule for daily stimulation. An included bi-directional telemetry link in the system can inform the patient or clinician of the status of the system, including the state of charge of the IPG battery. Other processing circuitry in the IPG allows electrode impedance measurements to be made. Circuitry provided in the external battery charger can provide alignment detection for the coil pairs. FIG. 1 depicts a SCS system, as described herein, for use during the trial period and the permanent implantation.

The SCS system, as disclosed herein, is superior to existing SCS systems in that the SCS system, as disclosed herein, can provide a stimulus to a selected pair or group of a multiplicity of electrodes, e.g., 32 electrodes, grouped into multiple channels, e.g., 6 channels. In an embodiment, each electrode is able to produce a programmable constant output current of at least 12 mA over a range of output voltages that may go as high as 16 volts. In another embodiment, the implant portion of the SCS system includes a rechargeable power source, e.g., one or more rechargeable batteries. The SCS system described herein requires only an occasional recharge, has an implanted portion smaller than existing implant systems, has a self-aligning feature to guide the patient in aligning the charger over the implanted IPG for the most efficient power recharge, has a life of at least 10 years at typical settings, offers a simple connection scheme for detachably connecting a lead system thereto, and is extremely reliable.

In an embodiment, each of the electrodes included within the stimulus channels can deliver up to 12.7 mA of current over the entire range of output voltages, and can be combined with other electrodes to deliver current up to a maximum of 20 mA. Additionally, the SCS system provides the ability to stimulate simultaneously on all available electrodes in the SCS system. That is, in operation, each electrode can be grouped with at least one additional electrode to form one channel. The SCS system allows the activation of electrodes to at least 10 channels. In one embodiment, such grouping is achieved by a low impedance switching matrix that allows any electrode contact or the system case (which may be used as a common, or indifferent, electrode) to be connected to any other electrode. In another embodiment, programmable output current DAC's (digital-to-analog converters) are connected to each electrode node, so that, when enabled, any electrode node can be grouped with any other electrode node that is enabled at the same time, thereby eliminating the need for a low impedance switching matrix. This advantageous feature allows the clinician to provide unique electrical stimulation fields for each current channel, heretofore unavailable with other "multichannel" stimulation systems (which "multi-channel" stimulation systems are really multiplexed single channel stimulation systems). Moreover, this feature, combined with multicontact electrodes arranged in two or three dimensional arrays, allows "virtual electrodes" to be realized, where a "virtual electrode" comprises an electrode that appears to be at a certain physical location, but in actuality is not physically located at the certain physical location. Rather, the "virtual electrode" results from the vector combination of electrical fields from two or more electrodes that are activated simultaneously.

In embodiments, the SCS system includes an implantable pulse generator (IPG) powered by a rechargeable internal battery, e.g., a rechargeable lithium ion battery providing an output voltage that varies from about 4.1 volts, when fully charged, to about 3.5 volts.

Embodiments are comprised of components previously not provided on SCS systems. The components are comprised of a number of different sub-components, as described herein. The SCS system can be comprised of a permanent implantable IPG, an implantable trial IPG, a wireless dongle, an IPG charger, clinical programmer software, patient programmer software, leads (percutaneous and paddle), lead anchors, lead splitters, lead extensions, and accessories. FIG. 1 depicts the components during trial and permanent implantation.

DETAILED DESCRIPTION

Implantable Pulse Generator (IPG)

Figure 1:
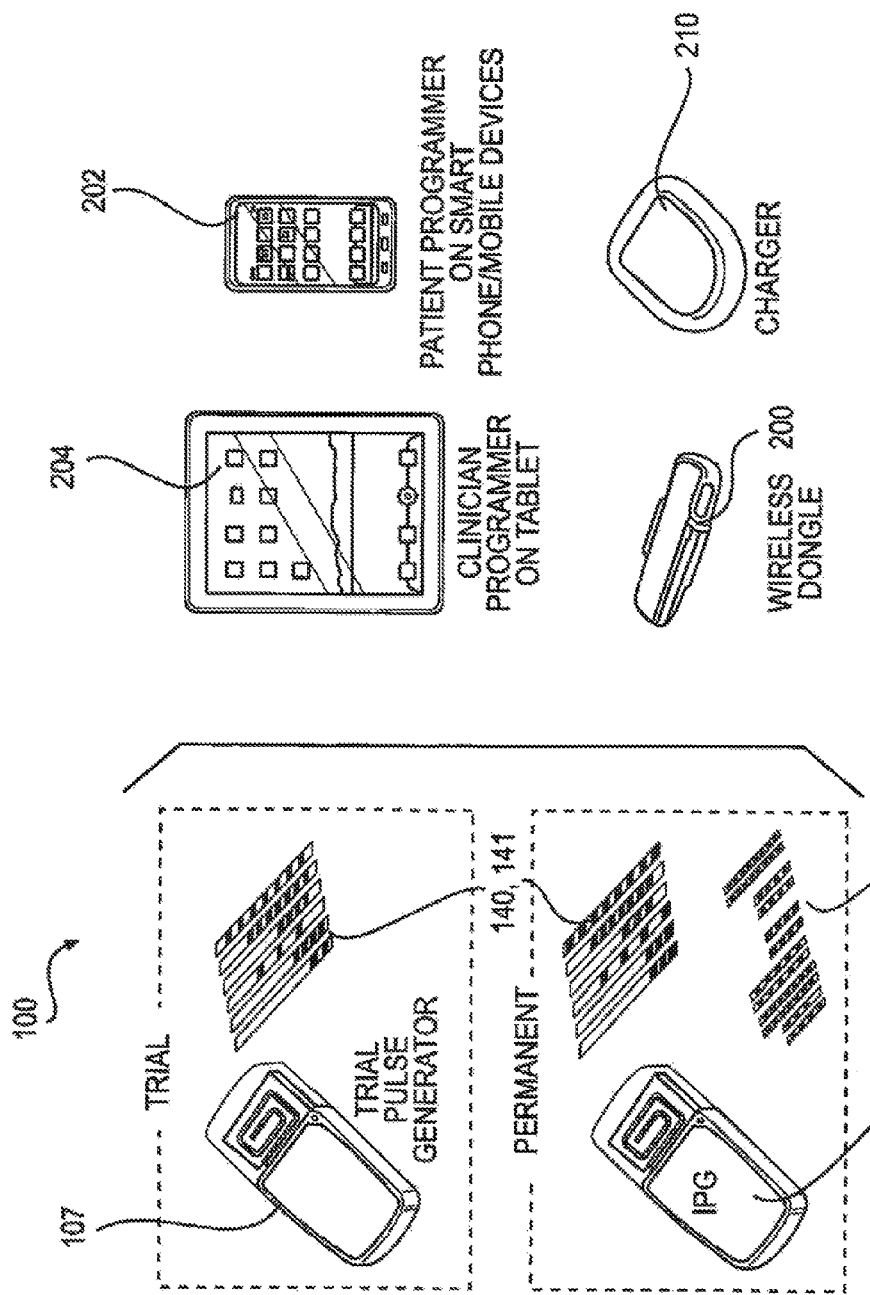
FIG. 1 depicts various components that can be included in a spinal cord stimulation system, according to an embodiment.

FIG. 1 illustrates various components that can be included in a SCS system for the trial and the permanent installation periods. The spinal cord stimulator (SCS) 100 is an implantable device used to deliver electrical pulse therapy to the spinal cord in order to treat chronic pain. The implantable components of the system consist of an Implantable Pulse Generator (IPG) 102 and a multitude of stimulation electrodes 130. The IPG 102 is implanted subcutaneously, no more than 30 mm deep in an area that is comfortable for the patient while the stimulation electrodes 130 are implanted directly in the epidural space. The electrodes 130 are wired to the IPG 102 via leads 140, 141 which keep the stimulation pulses isolated from each other in order to deliver the correct therapy to each individual electrode 130.

The therapy delivered consists of electrical pulses with controlled current amplitude ranging from +12.7 to −12.7 mA (current range 0-25.4 mA). These pulses can be programmed in both length and frequency from 10 μs to 2000 μs and 0.5 Hz to 1200 Hz. At any given moment, the sum of the currents sourced from the anodic electrodes 130 must equal the sum of the currents sunk by the cathodic electrodes 130. In addition, each individual pulse is bi-phasic, meaning that once the initial pulse finishes another pulse of opposite amplitude is generated after a set holdoff period. The electrodes 130 may be grouped into stimulation sets in order to deliver the pulses over a wider area or to target specific areas, but the sum of the currents being sourced at any one given time may not exceed 20 mA. A user can also program different stimulation sets (up to eight) with different parameters in order to target different areas with different therapies.

Figure 2:
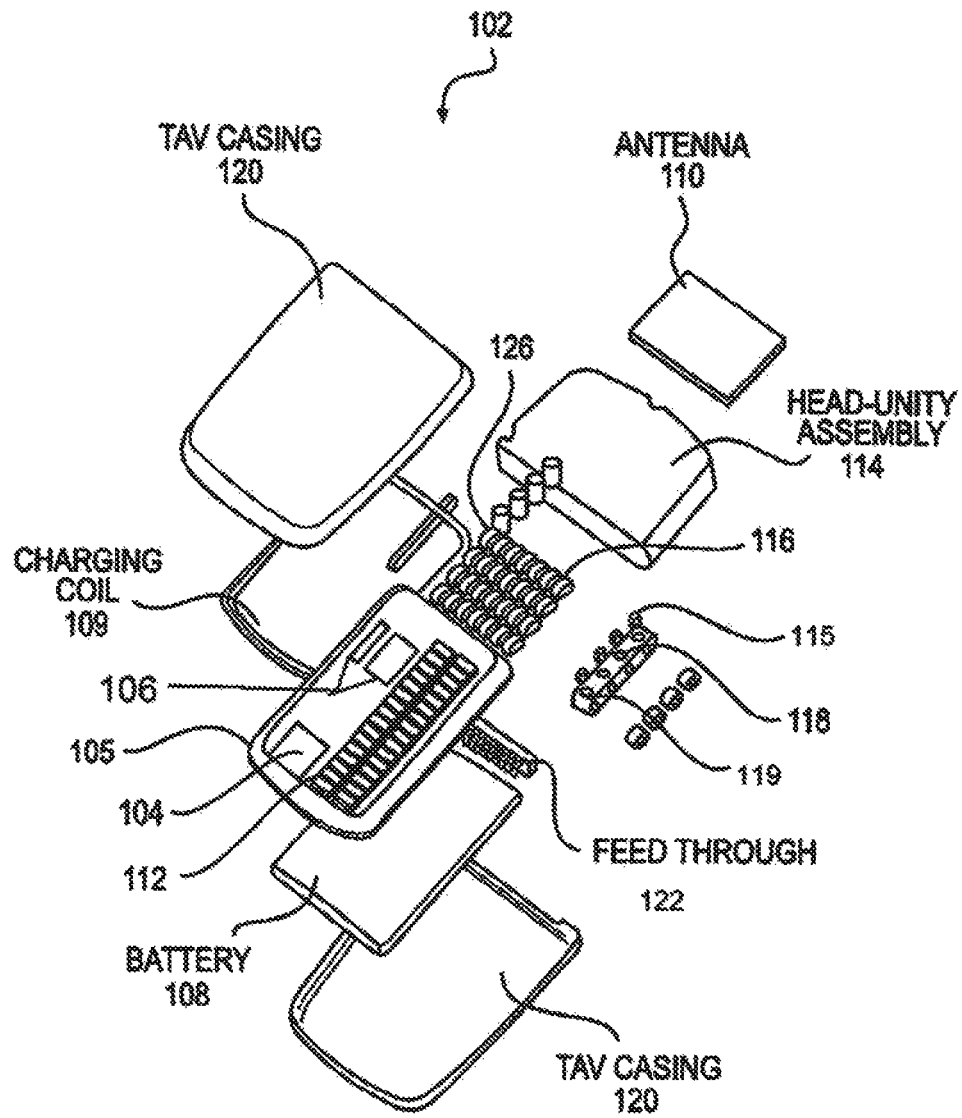
FIG. 2 depicts an exploded view of an implantable pulse generator (IPG) assembly, according to an embodiment.

FIG. 2 depicts an exploded view of an IPG 102. The IPG 102 consists of two major active components 104, 106, a battery 108, antenna 110, some support circuitry, and a multitude of output capacitors 112. The first of the major active components is the microcontroller transceiver 104. It is responsible for receiving, decoding, and execution both commands and requests from the external remote. If necessary it passes these commands or requests onto the second major component, the ASIC 106. The ASIC 106 receives the digital data from the microcontroller 104 and performs the entire signal processing to generate the signals necessary for stimulation. These signals are then passed onto the stimulation electrodes 130 in the epidural space.

The ASIC 106 is comprised of a digital section and an analog section. The digital section is divided into multiple sections including; Timing Generators, Arbitration Control, Pulse Burst Conditioner, and Electrode Logic. The analog section receives the incoming pulses from the digital section and amplifies them in order to deliver the correct therapy. There are also a multitude of digital register memory elements that each section utilizes, both digital and analog.

The digital elements in the ASIC 106 are all made up of standard subsets of digital logic including logic gates, timers, counters, registers, comparators, flip-flips, and decoders. These elements are ideal for processing the stimulation pulses as all of them can function extremely fast—orders of magnitudes faster than the required pulse width. The one drawback is that they must all function at one single voltage, usually 5.0, 3.3, 2.5, or 1.8 volts. Therefore they are not suitable for the final stage in which the pulses are amplified in order to deliver the constant current pulses.

The timing generators are the base of each of the stimulation sets. It generates the actual rising and falling edge triggers for each phase of the bi-phasic pulse. It accomplishes this by taking the incoming clock that is fed from the microcontroller 104 and feeding it into a counter. For the purpose of this discussion, assume the counter simply counts these rising clock edges infinitely. The output of the counter is fed into six different comparators. The comparators other input is connected to specific registers that are programmed by the microcontroller 104. When the count equals the value stored in the register, the comparator asserts a positive signal.

The first comparator is connected to the SET signal of a SR flip flop. The SR flip flop stays positive until the RESET signal is asserted, which the second comparator is connected to. The output of the SR flip flop is the first phase of the bi-phasic pulse. Its rising & falling edges are values stored in the registers and programmed by the microcontroller 104. The third and fourth comparators & registers work in exactly the same way to produce the second phase of the bi-phasic pulse using the second SR flip flop.

The fifth comparator is connected the RESET of the final SR-Flip flop in the timing generator. This flip flop is SET by the first comparator, which is the rising edge of the first pulse. The RESET is then triggered by the value the microprocessor programmed into the register connected to the comparator. This allows for a 'holdoff' period after the falling edge of the second pulse. The output of this third SR flip flop can be thought of as an envelope of the biphasic pulses indicating when this particular timing generator is active.

The final comparator of the system is once again connected to a register that stores the frequency values from the microprocessor. Essentially when the count reaches this value it triggers the comparator which is fed back to the counter to reset it to zero and beginning the entire pulse generation cycle again. The ASIC 106 may contain many of these timing generators as each can control anywhere from two to all of the electrodes 130 connected to the IPG 102 at a time. However, when there is more than one timing generator and multiple channels have been actively programmed then there needs to be a mechanism for suppressing a second channel from turning on when another is already active.

This brings us to the next circuit block contained in the IPG 102, the arbitrator. The arbitrator functions by looking at each of the timing generators' envelope signals and makes sure only one can be active at a time. If a second tries to activate then the arbitrator suppresses that signal.

It accomplishes this by bringing each of the channel envelope signals into a rising edge detection circuit. Once one is triggered it is fed into the SET pin of an SR flip flop. The output of this SR-flip flop is fed into all of the other rising edge detectors in order to suppress them from triggering. The channel envelope signal is also fed into a falling-edge detector which is then fed into the RESET of the same SR flip flop. The output of the SR flip flops are then connected to switches whose outputs are all tied together that turn on/off that channels particular biphasic pulse train. Therefore the output of this circuit element is a single bi-phasic pulse train and a signal designating which timing generator that particular pulse train is sourced from. Essentially, the circuit looks for a channel to go active. Once it finds one it suppresses all others until that channel becomes inactive.

The next section of the circuit works very similarly to the timing generators to create a high speed burst pulse train that is then combined with the stimulation pulse train to create a bursted bi-phasic pulse train if desired.

It accomplishes this by taking the incoming clock that is fed from the microcontroller 104 and feeding it into a counter. For the purpose of this discussion, assume the counter simply counts these rising clock edges infinitely. The counter is only active when during a single phase of the bi-phasic signal and begins counting as soon as the rising edge is detected. The output of the counter is fed into a comparator, along with a microcontroller-programmed register, whose output is connected to the reset pin on the counter. Therefore this counter will simply count to a programmed value & reset. This programmed value is the burst frequency.

The output of the comparator is then fed into an edge detection circuit and then a flip flop that combines it with the actual stimulation pulse train to create a single phase bursted stimulation pulse. The entire circuit is duplicated for the second phase of the signal resulting in the desired bursted bi-phasic pulse train. The stimulation signal is now ready to be handed over to the electrode logic stage.

The electrode logic conditions and directs the bi-phasic signals to the analog section of the ASIC 106. At this point, the bi-phasic signals contain all of the pertinent timing information, but none of the required amplitude information. The incoming signals include the bi-phasic pulse train and another signal designating which timing generator the current active train came from. Each electrode logic cell has a register for each timing generator that stores this particular electrode's 130 amplitude values for that timing generator. The electrode logic cell uses the designation signal to determine which register to pull the amplitude values from, e.g. if the third timing generator is passed through the arbitration circuit then the electrode logic would read the value from the third register.

Once the value is pulled from the register, it goes through a series of logic gates. The gates first determine that the electrode 130 should be active. If not, they proceed no further and do not activate the analog section of the electrode output, thereby saving precious battery 108 power. Next they determine if this particular electrode 130 is an anode or cathode. If it is deemed to be an anode, the electrode logic passes the amplitude information and the biphasic signal to the positive current (digital to analog converter) DAC in the analog section of the ASIC 106. If it is deemed to be a cathode, the electrode logic passes the amplitude information and the biphasic signal to the negative current DAC in the analog section of the ASIC 106. The electrode logic circuit must make these decisions for each phase of the bi-phasic signal as every electrode 130 will switch between being an anode and a cathode.

The analog elements in the ASIC 106 are uniquely designed in order to produce the desired signals. The basis of analog IC design is the field effect transistor (FET) and the type of high current multiple output design required in SCS 100 means that the bulk of the silicon in the ASIC 106 will be dedicated to the analog section.

The signals from the electrode output are fed into each current DAC when that specific electrode 130 should be activated. Each electrode 130 has a positive and a negative current DAC, triggered by the electrode logic and both are never active at the same time. The job of each current DAC is, when activated, to take the digital value representing a stimulation current amplitude and produce an analog representation of this value to be fed into the output stage. This circuit forms half of the barrier between the digital and analog sections of the ASIC 106.

The digital section of the ASIC 106 is built upon a technology that only allows small voltages to exist. In moving to the analog section, the output of the current DAC (which is a low level analog signal) must be amplified to a higher voltage for use in the analog section. The circuit that performs this task is called a power level shifter. Because this circuit is built upon two different manufacturing technologies and requires high precision analog circuits built upon a digital base, it is extremely difficult to implement.

Once the voltages have been converted for usage in the analog portion of the ASIC 106 they are passed on to the output current stages. There are two current sources per electrode output. One will source a positive current and one will sink a negative current, but they will never both be active simultaneously. The current sources themselves are made up of analog elements similar to a Howland current source. There is an input stage, and amplification stage with feedback through a sensing component to maintain the constant current. The input stage takes the analog voltage values from the power level shifter and produces an output pulse designated for the amplifier. The amplifier then creates the pulses of varying voltages but constant current flow. The sources are capable of sourcing or sinking up to 12.7 mA at 0.1 mA resolution into a load of up to 1.2 k Ohms. This translates into range of 15 volts, which will vary depending on the load in order to keep the current constant.

The microcontroller 104 to ASIC 106 interface is designed to be as simple as possible with minimal bus 'chatter' in order to save battery 108 life. The ASIC 106 will essentially be a collection of registers programmed via a standard I$^2$C or SPI bus. Since the ASIC 106 is handling all the power management, there will also be a power good (PG) line between the two chips 104, 106 in order to let the microcontroller 104 know when it is safe to power up. The ASIC 106 will also need to use a pin on the microcontroller 104 in order to generate a hardware interrupt in case anything goes awry in the ASIC 106. The final connection is the time base for all of the stimulation circuitry. The ASIC 106 will require two clocks, one for its internal digital circuitry which will be fed directly from the microcontroller 104 clock output, and one to base all stimulation off of which will need to be synthesized by the microcontroller 104 and fed to the ASIC 106. All commands and requests to the ASIC 106 will be made over the I$^2$C or SPI bus and will involve simply reading a register address or writing to a register. Even when the ASIC 106 generates a hardware interrupt, it will be the responsibility of the microcontroller 104 to poll the ASIC 106 and determine the cause of the interrupt.

The wireless interface is based upon the FCCs MedRadio standard operating in the 402-405 Mhz range utilizing up to 10 channels for telemetry. The protocol is envisioned to be very simple once again in order to minimize transmission and maximize battery 108 life. All processing will take place on the user remote/programmer and the only data transmitted is exactly what will be used in the microcontroller 104 to ASIC 106 bus. That is, all of the wireless packets will contain necessary overhead information along with only a register address, data to store in the register, and a command byte instructing the microcontroller 104 what to do with the data. The overhead section of the wireless protocol will contain synchronization bits, start bytes, an address which is synchronized with the IPG's 102 serial number, and a CRC byte to assure proper transmission. It is essential to keep the packet length as small as possible in order to maintain battery 108 life. Since the IPG 102 cannot listen for packets all the time due to battery 108 life, it cycles on for a duty cycle of less than 0.05% of the time. This time value can be kept small as long as the data packets are also small. The user commands needed to run the system are executed by the entire system using flows.

The IPG 102 uses an implantable grade Li ion battery 108 with 215 mAHr with zero volt technology. The voltage of the battery 108 at full capacity is 4.1 V and it supplies current only until it is drained up to 3.3 V which is considered as 100% discharged. The remaining capacity of the battery 108 can be estimated at any time by measuring the voltage across the terminals. The maximum charge rate is 107.5 mA. A Constant Current, Constant Voltage (CCCV) type of regulation can be applied for faster charging of the battery 108.

The internal secondary coil 109 is made up of 30 turns of 30 AWG copper magnet wires. The ID, OD, and the thickness of the coil are 30, 32, and 2 mm, respectively. Inductance L2 is measured to be 58 uH, a 80 nF capacitor is connected to it to make a series resonance tank at 74 kHz frequency. In the art of induction charging, two types of rectifiers are considered to convert the induced AC into usable DC, either a bridge full wave rectifier or a voltage doubler full wave rectifier. To obtain a higher voltage, the voltage double full wave rectifier is used in this application. The rectifier is built with high speed Schottky diodes to improve its function at high frequencies of the order 100 kH. A Zener diode and also a 5V voltage regulator are used for regulation. This circuit will be able to induce AC voltage, rectify to DC, regulate to 5V and supply 100 mA current to power management IC that charges the internal battery 108 by CCCV regulation.

The regulated 5V 100 mA output from the resonance tank is fed to, for example, a Power Management Integrated Circuit (PMIC) MCP73843. This particular chip was specially designed by Microchip to charge a Li ion battery 108 to 4.1 V by CCCV regulation. The fast charge current can be regulated by changing a resistor; it is set to threshold current of 96 mA in this circuit. The chip charges the battery 108 to 4.1V as long as it receives current more than 96 mA. However, if the supply current drops below 96 mA, it stops to charge the battery 108 until the supply is higher than 96 again. For various practical reasons, if the distance between the coils increases, the internal secondary coil 109 receives lesser current than the regulated value, and instead of charging the battery 108 slowly, it pauses the charging completely until it receives more than 96 mA. It is understood to those with skill in the art that other power management chips can be used and the power management chip is not limited to the PMIC MCP738432 chip.

All the functions of the IPG 102 are controlled from outside using a hand held remote controller specially designed for this device. Along with the remote control, an additional control is desirable to operate the IPG 102 if the remote control was lost or damaged. For this purpose a Hall effect based magnet switch was incorporated to either turn ON or turn OFF the IPG 102 using an external piece of magnet. Magnet switch acts as a master control for the IPG 102 to turn on or off. A south pole of sufficient strength turns the output on and a north pole of sufficient strength is necessary to turn the output off. The output is latched so that the switch continues to hold the state even after the magnet is removed from its vicinity.

The IPG 102 is an active medical implant that generates an electrical signal that stimulates the spinal cord. The signal is carried through a stimulation lead 140 that plugs directly into the IPG 102. The IPG 102 recharges wirelessly through an induction coil 109, and communicates via RF radio antenna 110 to change stimulation parameters. The IPG 102 is implanted up to 3 cm below the surface of the skin and is fixed to the fascia by passing two sutures through holes in the epoxy header 114. The leads 140 are electrically connected to the IPG 102 through a lead contact system 116, a cylindrical spring-based contact system with inter-contact silicone seals. The leads 140 are secured to the IPG 102 with a set screw 117 that actuates within locking housing 118. Set screw compression on the lead's 140 fixation contact is governed by a disposable torque wrench. The wireless recharging is achieved by aligning the exterior induction coil on the charger with the internal induction coil 109 within the IPG 102. The RF antenna within the remote's dongle 200 communicates with the RF antenna 110 in the IPG's 102 epoxy header 114. FIG. 2 illustrates an exploded view of the IPG 102 assembly.

Figure 3:
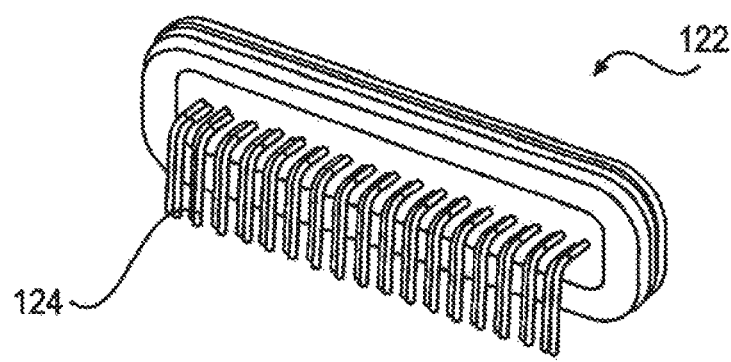
FIG. 3 depicts a feed through assembly of an implantable pulse generator (IPG) assembly, according to an embodiment.

The IPG 102 is an assembly of a hermetic titanium (6Al-4V) casing 120 which houses the battery 108, circuitry 104, 106, and charging coil 109, with an epoxy header 114, which houses the lead contact assembly 116, locking housing 118, and RF antenna 110. The internal electronics are connected to the components within the epoxy head through a hermetic feedthrough 122, as shown in FIG. 3. The feedthrough 122 is a titanium (6Al-4V) flange with an alumina window and gold trimming. Within the alumina window are thirty-four platinum-iridium (90-10) pins that interface internally with a direct solder to the circuit board, and externally with a series of platinum iridium wires laser-welded to the antenna 110 and lead contacts 126. The IPG 102 has the ability to interface with 32 electrical contacts 126, which are arranged in four rows of eight contacts 126. Thirty-two of the feedthrough's 122 pins 124 will interface with the contacts 126, while two will interface with the antenna 110, one to the ground plane and one to the antenna 110 feed.

Figure 4:
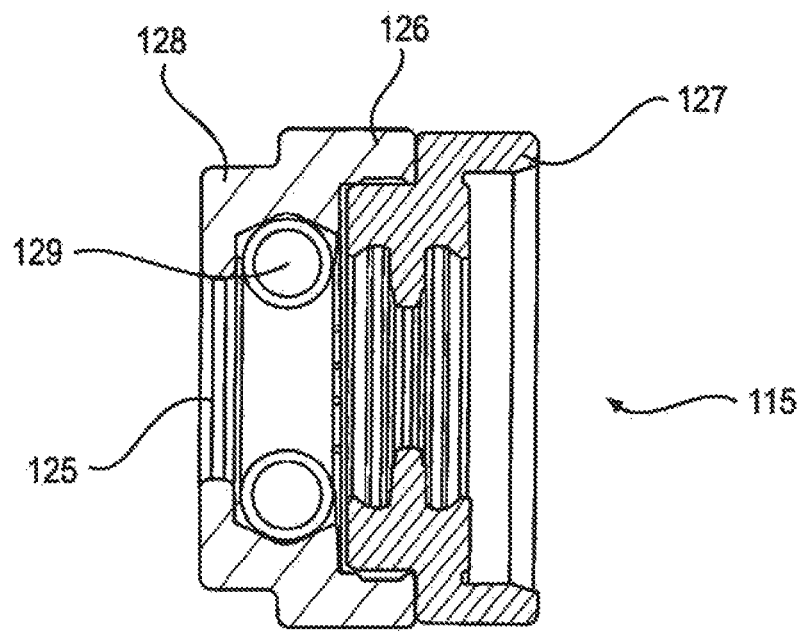
FIG. 4 depicts a lead contact system of an implantable pulse generator (IPG) assembly, according to an embodiment.
Figure 5:
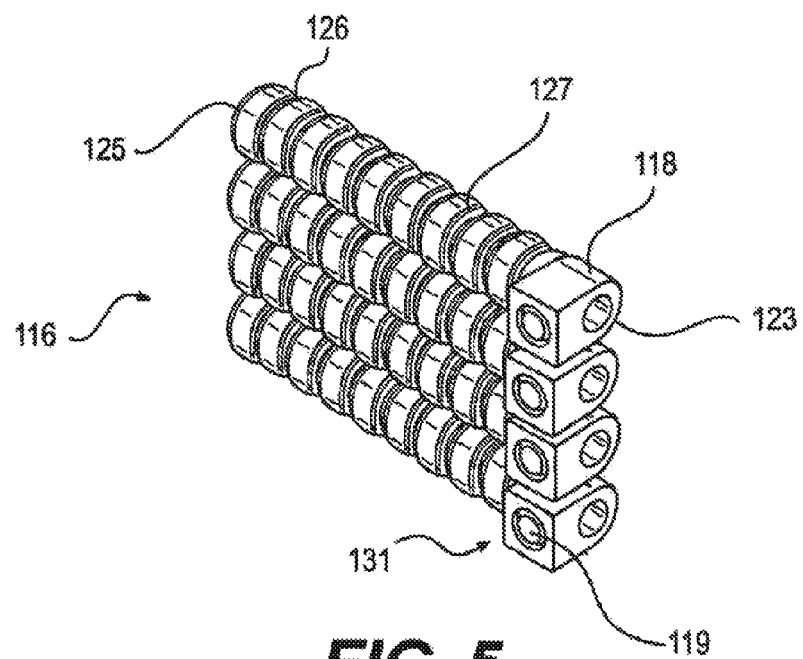
FIG. 5 depicts a lead contact assembly of an implantable pulse generator (IPG) assembly, according to an embodiment.
Figure 6:
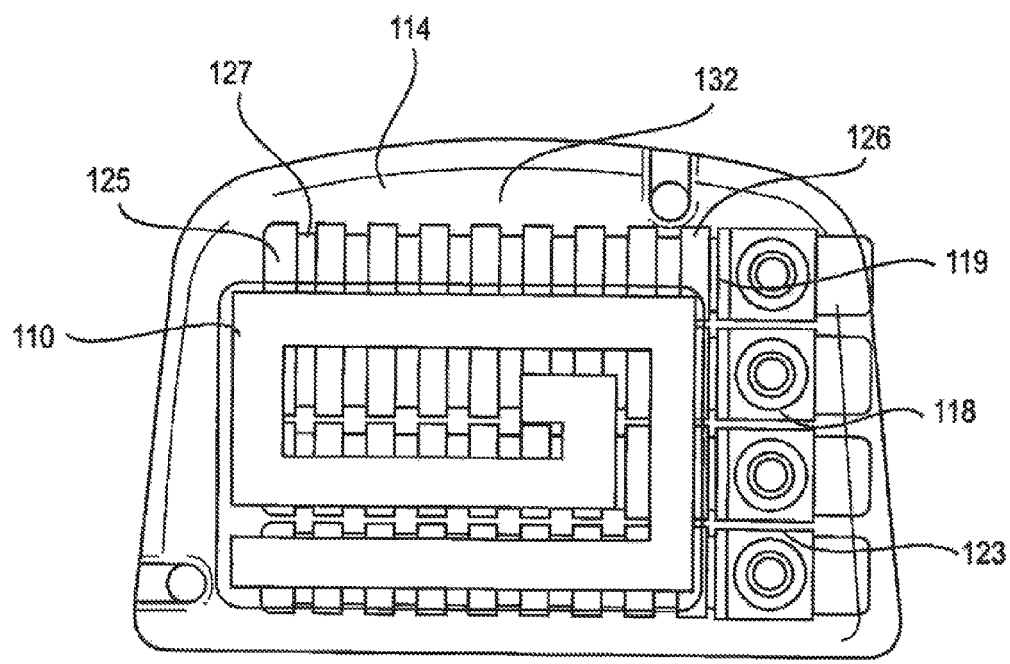
FIG. 6 depicts a head unit assembly of an implantable pulse generator (IPG) assembly, according to an embodiment.
Figure 7:
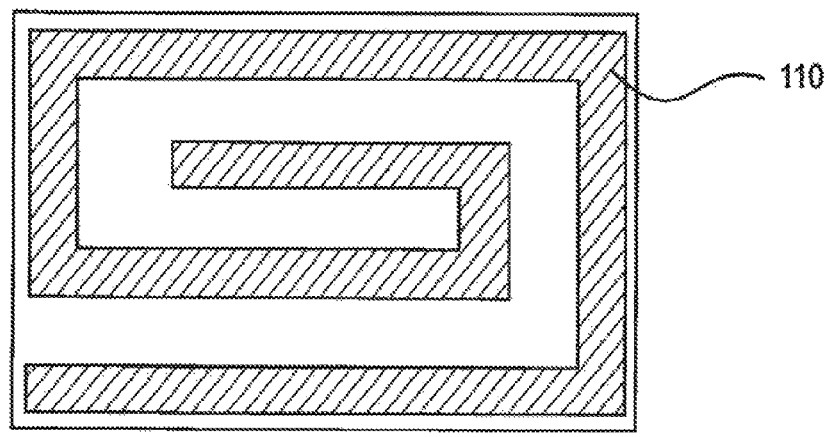
FIG. 7 depicts an RF antenna of an implantable pulse generator (IPG) assembly, according to an embodiment.

FIGS. 4 and 5 depict a lead contact system 115 and assembly 116, respectively. The lead contacts 126 consist of an MP35N housing 128 with a platinum-iridium 90-10 spring 129. Each contact 126 is separated by a silicone seal 127. At the proximal end of each stack of 8 contacts 126 is a titanium (6Al-4V) cap 125 which acts as a stop for the lead 140. At the distal end is a titanium (6Al-4V) set screw 119 and block 118 for lead fixation. At the lead entrance point there is a silicone tube 123 which provides strain relief as the lead 140 exits the head unit 114, and above the set screw 119 is another silicone tube 131 with a small internal canal which allows the torque wrench to enter but does not allow the set screw 119 to back out. In addition to the contacts 126 and antenna 110, the header 114 also contains a radiopaque titanium (6Al-4V) tag 132 which allows for identification of the device under fluoroscopy. The overmold of the header 114 is Epotek 301, a two-part, biocompatible epoxy. FIGS. 4, 5, 6, and 7 depict illustrations of lead contact system 115, lead contact assembly 116, head unit assembly 114, and RF antenna 110, respectively.

Internal to the titanium (6Al-4V) case 120 are the circuit board 105, battery 108, charging coil 109, and internal plastic support frame. The circuit board 105 will be a multi-layered FR-4 board with copper traces and solder mask coating. Non-solder masked areas of the board will be electroless nickel immersion gold. The implantable battery 108, all surface mount components, ASIC 106, microcontroller 104, charging coil 109, and feedthrough 122 will be soldered to the circuit board 105. The plastic frame, made of either polycarbonate or ABS, will maintain the battery's 108 position and provide a snug fit between the circuitry 105 and case 120 to prevent movement. The charging coil 109 is a wound coated copper.

Leads

Figure 8:
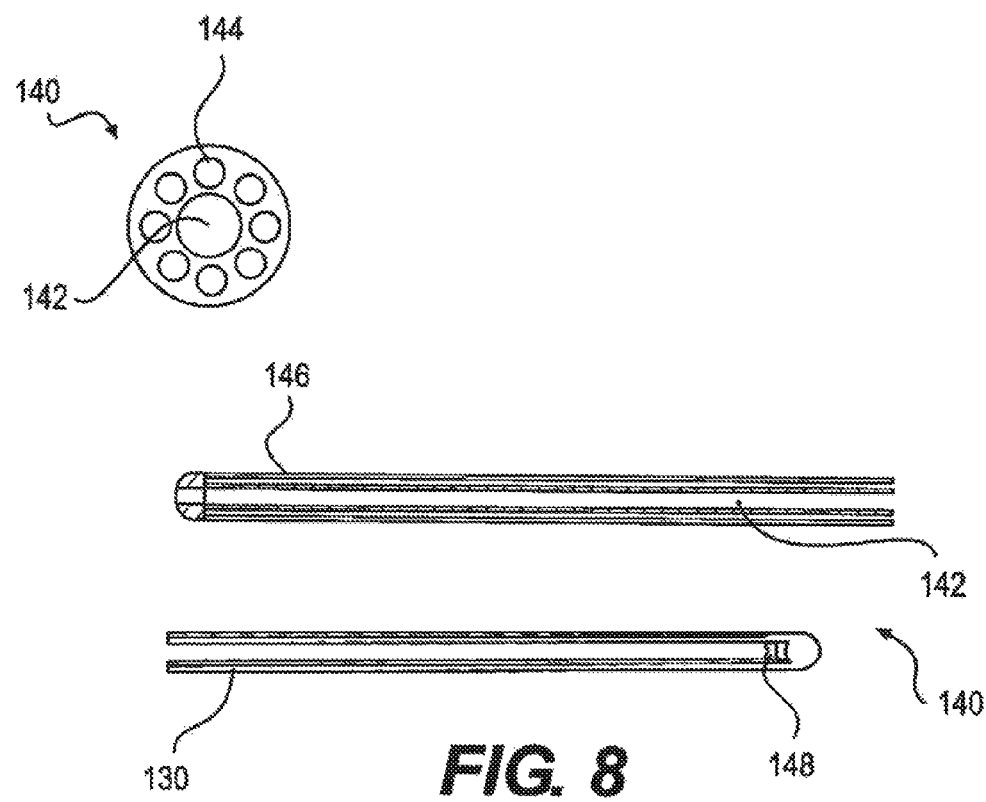
FIG. 8 depicts a percutaneous lead, according to an embodiment.

The percutaneous stimulation leads 140, as depicted in FIG. 8, are a fully implantable electrical medical accessory to be used in conjunction with the implantable SCS 100. The primary function of the lead is to carry electrical signals from the IPG 102 to the target stimulation area on the spinal cord. Percutaneous stimulation leads 140 provide circumferential stimulation. The percutaneous stimulation leads 140 must provide a robust, flexible, and bio-compatible electric connection between the IPG 102 and stimulation area. The leads 140 are surgically implanted through a spinal needle, or epidural needle, and are driven through the spinal canal using a steering stylet that passes through the center of the lead 140. The leads 140 are secured mechanically to the patient using either an anchor or a suture passed through tissue and tied around the body of the lead 140. The leads 140 are secured at the proximal end with a set-screw 119 on the IPG 102 which applies radial pressure to a blank contact on the distal end of the proximal contacts.

The percutaneous stimulation leads 140 consist of a combination of implantable materials. Stimulation electrodes 130 at the distal end and electrical contacts at the proximal end are made of a 90-10 platinum-iridium alloy. This alloy is utilized for its bio-compatibility and electrical conductivity. The electrodes 130 are geometrically cylindrical. The polymeric body of the lead 140 is polyurethane, which is chosen for its bio-compatibility, flexibility, and high lubricity to decrease friction while being passed through tissue. The polyurethane tubing has a multi-lumen cross section, with one center lumen 142 and eight outer lumens 144. The center lumen 142 acts as a canal to contain the steering stylet during implantation, while the outer lumens 144 provide electrical and mechanical separation between the wires 146 that carry stimulation from the proximal contacts to distal electrodes 130. These wires 146 are a bundle of MP35N strands with a 28% silver core. The wires 146 are individually coated with ethylene tetrafluoroethylene (ETFE), to provide an additional non-conductive barrier. The wires 146 are laser welded to the contacts and electrodes 130, creating an electrical connection between respective contacts on the proximal and distal ends. The leads 140 employ a platinum-iridium plug 148, molded into the distal tip of the center lumen 142 to prevent the tip of the steering stylet from puncturing the distal tip of the lead 140. Leads 140 are available in a variety of 4 and 8 electrode 130 configurations. These leads 140 have 4 and 8 proximal contacts (+1 fixation contact), respectively. Configurations vary by electrode 130 number, electrode 130 spacing, electrode 130 length, and overall lead 140 length.

Figure 9:
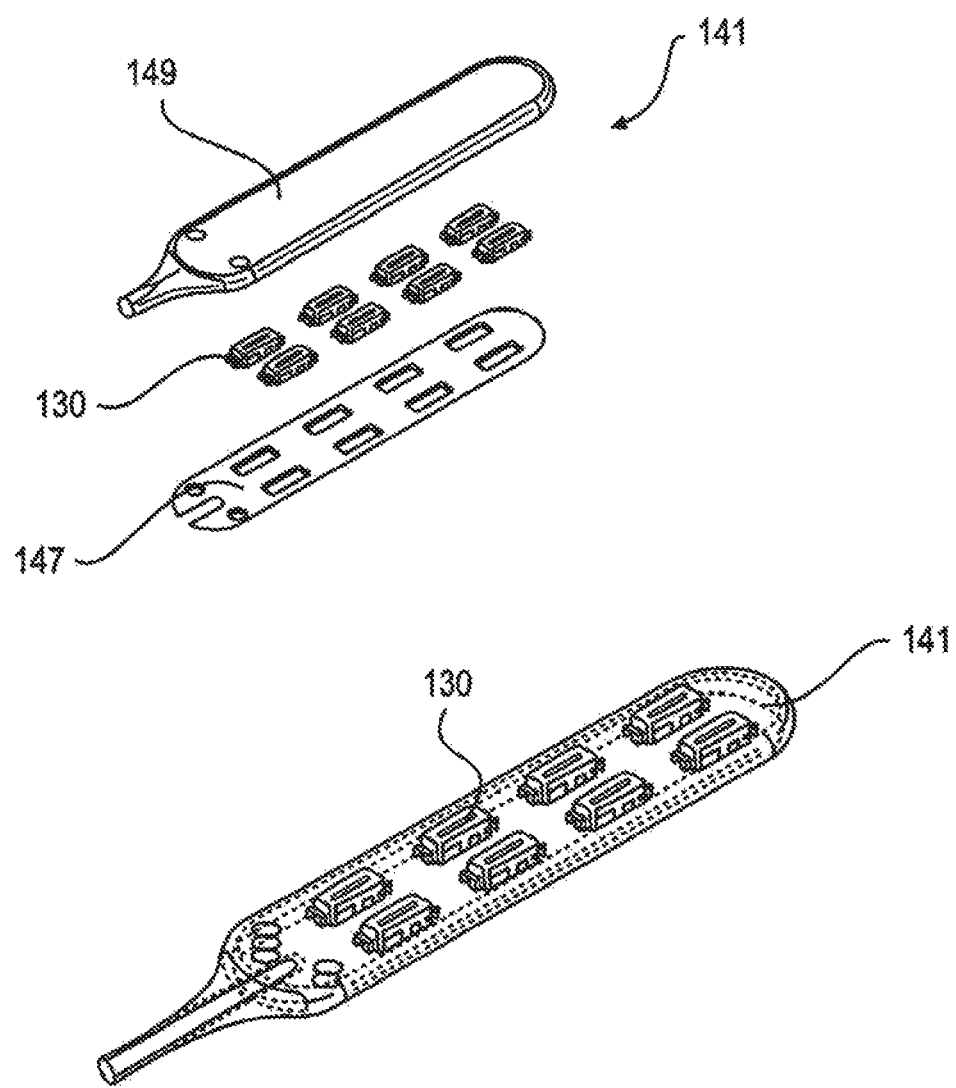
FIG. 9 depicts a paddle lead, according to an embodiment.

The paddle stimulation leads 141, as depicted in FIG. 9, are a fully implantable electrical medical accessory to be used in conjunction with the implantable SCS 100. The primary function of the paddle lead 141 is to carry electrical signals from the IPG 102 to the target stimulation area on the spinal cord. The paddle leads 141 provide uni-direction stimulation across a 2-dimensional array of electrodes 130, allowing for greater precision in targeting stimulation zones. The paddle stimulation leads 141 must provide a robust, flexible, and bio-compatible electric connection between the IPG 102 and stimulation area. The leads 141 are surgically implanted through a small incision, usually in conjunction with a laminotomy or laminectomy, and are positioned using forceps or a similar surgical tool. The leads 141 are secured mechanically to the patient using either an anchor or a suture passed through tissue and tied around the body of the lead 141. The leads 141 are secured at the proximal end with a set-screw on the IPG 102 which applies radial pressure to a fixation contact on the distal end of the proximal contacts.

The paddle stimulation leads 141 consist of a combination of implantable materials. Stimulation electrodes 130 at the distal end and electrical contacts at the proximal end are made of a 90-10 platinum-iridium alloy. This alloy is utilized for its bio-compatibility and electrical conductivity. The polymeric body of the lead 141 is polyurethane, which is chosen for its bio-compatibility, flexibility, and high lubricity to decrease friction while being passed through tissue. The polyurethane tubing has a multi-lumen cross section, with one center lumen 142 and eight outer lumens 144. The center lumen 142 acts as a canal to contain the steering stylet during implantation, while the outer lumens 144 provide electrical and mechanical separation between the wires 146 that carry stimulation from the proximal contacts to distal electrodes 130. These wires 146 are a bundle of MP35N strands with a 28% silver core. The wires 146 are individually coated with ethylene tetrafluoroethylene (ETFE), to provide an additional non-conductive barrier. At the distal tip of the paddle leads 141, there is a 2-dimensional array of flat rectangular electrodes 130, molded into a flat silicone body 149. Only one side of the rectangular electrodes 130 is exposed, providing the desired uni-directional stimulation. The wires 146 are laser welded to the contacts and electrodes 130, creating an electrical connection between respective contacts on the proximal and distal ends. Also molded into the distal silicone paddle is a polyester mesh 147 which adds stability to the molded body 149 while improving aesthetics by covering wire 146 routing. The number of individual 8-contact leads 141 used for each paddle 141 is governed by the number of electrodes 130. Electrodes 130 per paddle 141 range from 8 to 32, which are split into between one and four proximal lead 141 ends. Each proximal lead 141 has 8 contacts (+1 fixation contact). Configurations vary by electrode 130 number, electrode 130 spacing, electrode length, and overall lead length.

Figure 10:
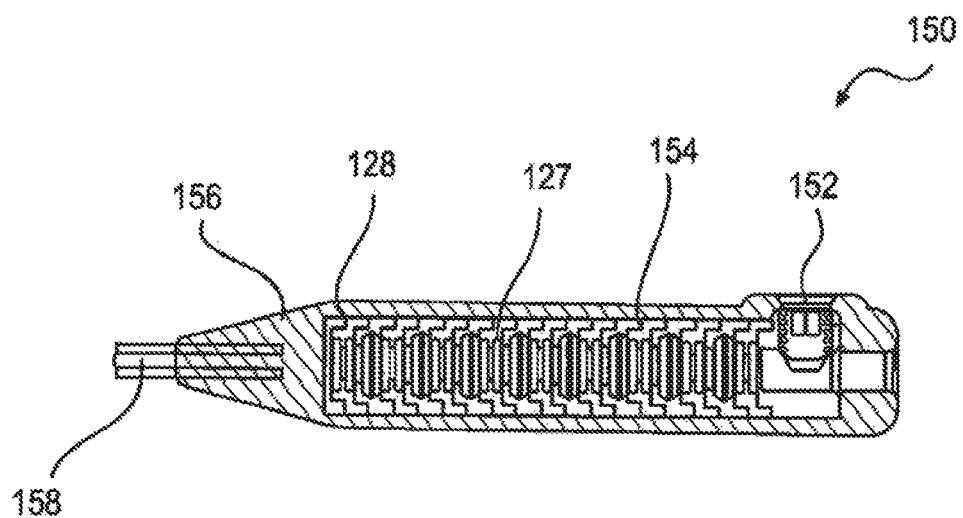
FIG. 10 depicts a lead extension, according to an embodiment.

The lead extensions 150, as depicted in FIG. 10, are a fully implantable electrical medical accessory to be used in conjunction with the implantable SCS 100 and either percutaneous 140 or paddle 141 leads. The primary function of the lead extension 150 is to increase the overall length of the lead 140, 141 by carrying electrical signals from the IPG 102 to the proximal end of the stimulation lead 140, 141. This extends the overall range of the lead 140, 141 in cases where the length of the provided leads 140, 141 is insufficient for case. The lead extensions 150 must provide a robust, flexible, and bio-compatible electric connection between the IPG 102 and proximal end of the stimulation lead 140, 141. The extensions 150 may be secured mechanically to the patient using either an anchor or a suture passed through tissue and tied around the body of the extension 150. Extensions 150 are secured at the proximal end with a set-screw 119 on the IPG 102 which applies radial pressure to a fixation contact on the distal end of the proximal contacts of the extension 150. The stimulation lead 140, 141 is secured to the extension 150 in a similar fashion, using a set screw 152 inside the molded tip of extension 150 to apply a radial pressure to the fixation contact at the proximal end of the stimulation lead 140, 141.

The lead extension 150 consists of a combination of implantable materials. At the distal tip of the extension 150 is a 1×8 array of implantable electrical contacts 154, each consisting of MP35 housing 128 and 90-10 platinum-iridium spring. A silicone seal 127 separates each of the housings 128. At the proximal end of the contacts is a titanium (6Al4V) cap which acts as a stop for the lead, and at the distal tip, a titanium (6Al4V) block and set screw 152 for lead fixation. The electrical contacts at the proximal end are made of a 90-10 platinum-iridium alloy. This alloy is utilized for its bio-compatibility and electrical conductivity. The polymeric body 156 of the lead 150 is polyurethane, which is chosen for its bio-compatibility, flexibility, and high lubricity to decrease friction while being passed through tissue. The polyurethane tubing 158 has a multi-lumen cross section, with one center lumen 142 and eight outer lumens 144. The center lumen 142 acts as a canal to contain the steering stylet during implantation, while the outer lumens 144 provide electrical and mechanical separation between the wires 146 that carry stimulation from the proximal contacts to distal electrodes. These wires 146 are a bundle of MP35N strands with a 28% silver core. The wires 146 are individually coated with ethylene tetrafluoroethylene (ETFE), to provide an additional non-conductive barrier. Each lead extension 150 has 8 proximal cylindrical contacts (+1 fixation contact).

Figure 11:
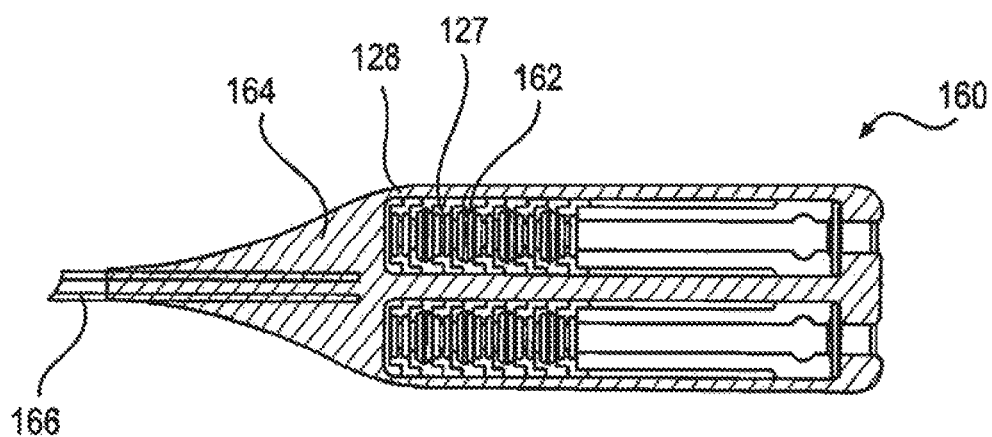
FIG. 11 depicts a lead splitter, according to an embodiment.

The lead splitter 160, as depicted in FIG. 11, is a fully implantable electrical medical accessory which is used in conjunction with the SCS 100 and typically a pair of 4-contact percutaneous leads 140. The primary function of the lead splitter 160 is to split a single lead 140 of eight contacts into a pair of 4 contact leads 140. The splitter 160 carries electrical signals from the IPG 102 to the proximal end of two 4-contact percutaneous stimulation leads 140. This allows the surgeon access to more stimulation areas by increasing the number of stimulation leads 140 available. The lead splitter 160 must provide a robust, flexible, and bio-compatible electrical connection between the IPG 102 and proximal ends of the stimulation leads 140. The splitters 160 may be secured mechanically to the patient using either an anchor or a suture passed through tissue and tied around the body of the splitter 160. Splitters 160 are secured at the proximal end with a set-screw 119 on the IPG 102 which applies radial pressure to a fixation contact on the distal end of the proximal contacts of the splitter 160. The stimulation leads 140 are secured to the splitter 160 in a similar fashion, using a pair of set screws inside the molded tip of splitter 160 to apply a radial pressure to the fixation contact at the proximal end of each stimulation lead 140.

The lead splitter 160 consists of a combination of implantable materials. At the distal tip of the splitter 160 is a 2×4 array of implantable electrical contacts 162, with each contact 162 consisting of MP35 housing 128 and 90-10 platinum-iridium spring. A silicone seal 127 separates each of the housings 128. At the proximal end of each row of contacts 162 is a titanium (6Al4V) cap which acts as a stop for the lead, and at the distal tip, a titanium (6Al4V) block and set screw for lead fixation. The electrical contacts at the proximal end of the splitter 160 are made of a 90-10 platinum-iridium alloy. This alloy is utilized for its biocompatibility and electrical conductivity. The polymeric body 164 of the lead 160 is polyurethane, which is chosen for its bio-compatibility, flexibility, and high lubricity to decrease friction while being passed through tissue. The polyurethane tubing 166 has a multi-lumen cross section, with one center lumen 142 and eight outer lumens 144. The center lumen 142 acts as a canal to contain the steering stylet during implantation, while the outer lumens 144 provide electrical and mechanical separation between the wires 146 that carry stimulation from the proximal contacts to distal electrodes 130. These wires 146 are a bundle of MP35N strands with a 28% silver core. The wires 146 are individually coated with ethylene tetrafluoroethylene (ETFE), to provide an additional non-conductive barrier. Each lead splitter 160 has 8 proximal contacts (+1 fixation contact), and 2 rows of 4 contacts 162 at the distal end.

Anchors

Figure 12:
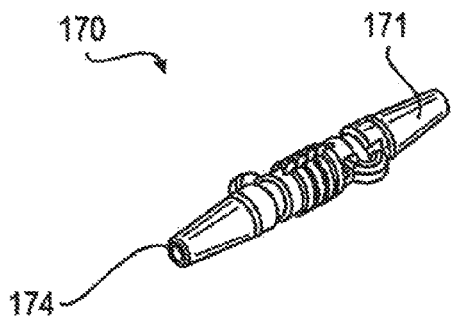
FIG. 12 depicts a sleeve anchor, according to an embodiment.
Figure 13:
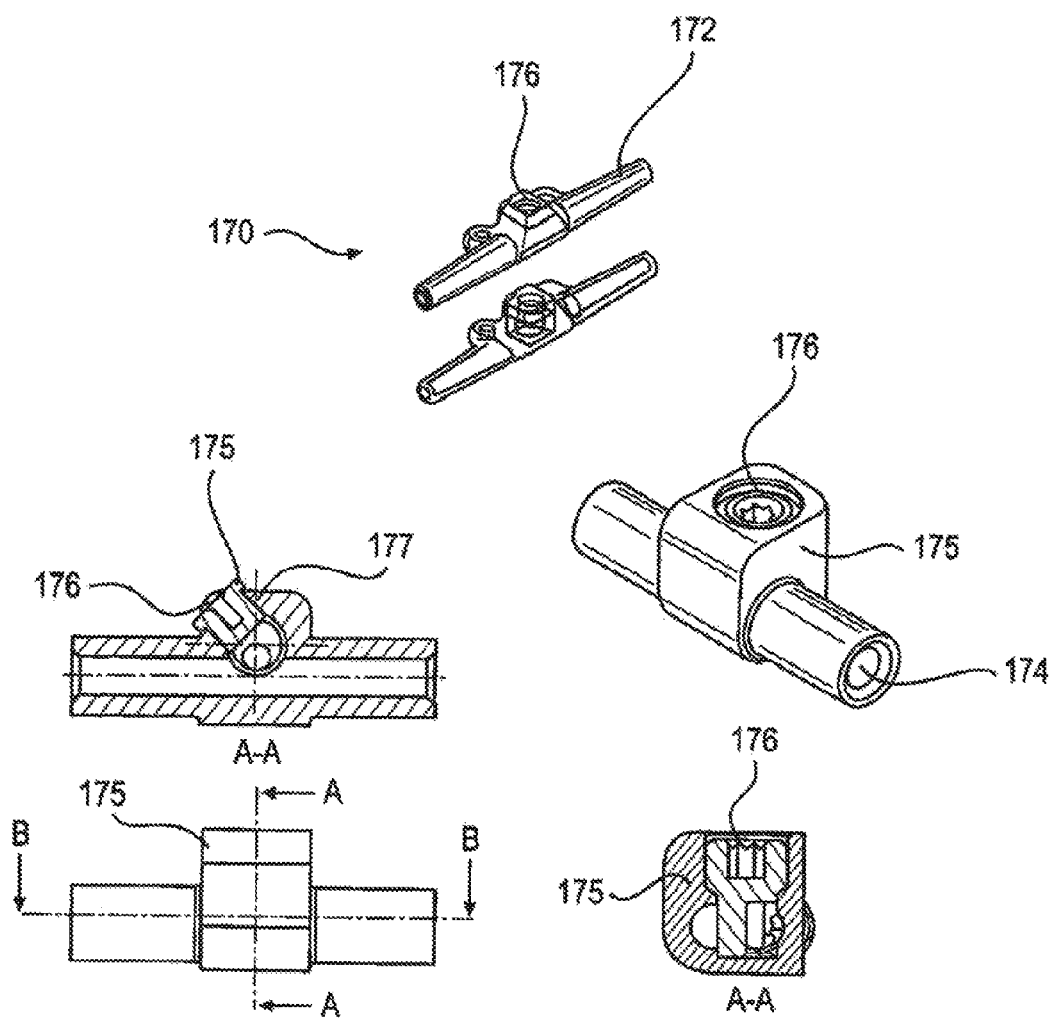
FIG. 13 depicts a mechanical locking anchor, according to an embodiment.

The lead anchor 170, as depicted in FIGS. 12 and 13, is a fully implantable electrical medical accessory which is used in conjunction with both percutaneous 140 and paddle 141 stimulation leads. The primary function of the lead anchor 170 is to prevent migration of the distal tip of the lead 140, 141 by mechanically locking the lead 140, 141 to the tissue. There are currently two types of anchors 170, a simple sleeve 171, depicted in FIG. 12, and a locking mechanism 172, depicted in FIG. 13, and each has a slightly different interface. For the simple sleeve type anchor 171, the lead 140, 141 is passed through the center thru-hole 174 of the anchor 171, and then a suture is passed around the outside of the anchor 171 and tightened to secure the lead 140, 141 within the anchor 171. The anchor 171 can then be sutured to the fascia. The locking anchor 172 uses a set screw 176 for locking purposes, and a bi-directional disposable torque wrench for locking and unlocking. Tactile and audible feedback is provided for both locking and unlocking.

Both anchors 171, 172 are molded from implant-grade silicone, but the locking anchor 172 uses an internal titanium assembly for locking. The 3-part mechanism is made of a housing 175, a locking set screw 176, and a blocking set screw 177 to prevent the locking set screw from back out. All three components are titanium (6Al4V). The bi-directional torque wrench has a plastic body and stainless steel hex shaft.

Wireless Dongle

Figure 14:
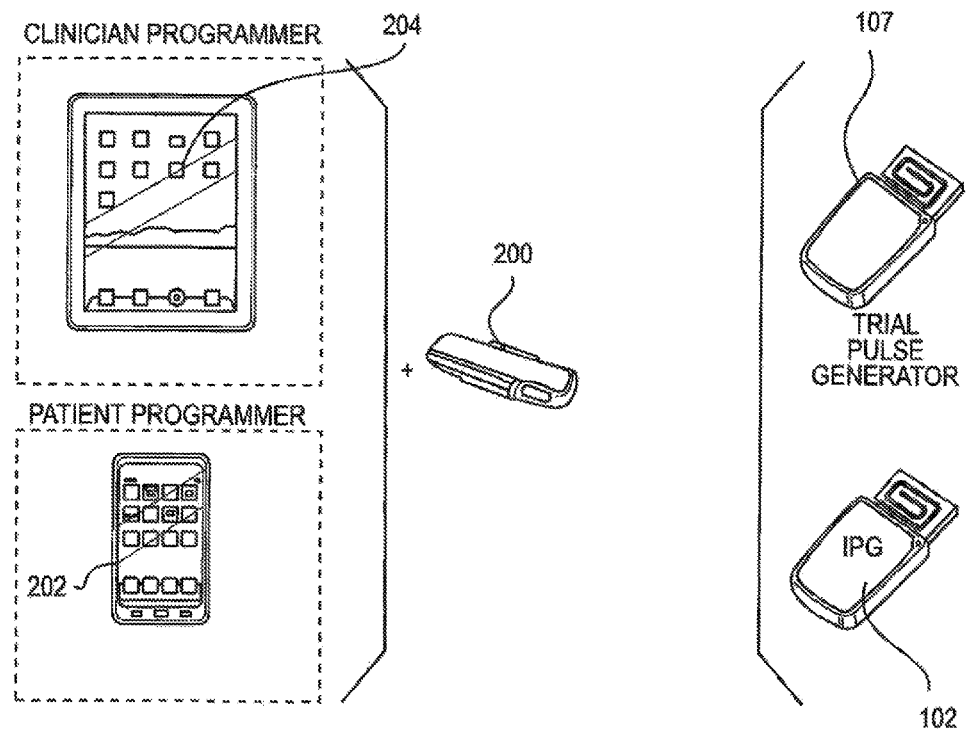
FIG. 14 illustrates communication via a wireless dongle with a tablet/clinician programmer and smartphone/mobile/patient programmer during trial and/or permanent implantation, according to an embodiment.

The wireless dongle 200 is the hardware connection to a smartphone/mobile 202 or tablet 204 that allows communication between the trial generator 107 or IPG 102 and the smartphone/mobile device 202 or tablet 204, as illustrated in FIG. 14. During the trial or permanent implant phases, the wireless dongle 200 is connected to the tablet 204 through the tablet 204 specific connection pins and the clinician programmer software on the tablet 204 is used to control the stimulation parameters. The commands from the clinician programmer software are transferred to the wireless dongle 200 which is then transferred from the wireless dongle 200 using RF signals to the trial generator 107 or the IPG 102. Once the parameters on the clinician programmers have been set, the parameters are saved on the tablet 204 and transferred to the patient programmer software on the smartphone/mobile device 202. The wireless dongle 200 is composed of an antenna, a microcontroller (having the same specifications as the IPG 102 and trial generator 107), and a pin connector to connect with the smartphone/mobile device 202 and the tablet 204.

Charger

The IPG 102 has a rechargeable Lithium ion battery 108 to power its activities. An external induction type charger 210 (FIG. 1) is necessary to recharge the included battery 108 inside the IPG 102 wirelessly. The charger 210 consists of a rechargeable battery, a primary coil of wire and a printed circuit board (PCB) for the electronics—all packaged into a housing. When switched on, this charger 210 produces magnetic field and induces voltage into the secondary coil 109 in the implant. The induced voltage is then rectified and then used to charge the battery 108 inside the IPG 102. To maximize the coupling between the coils, both internal and external coils are combined with capacitors to make them resonate at a particular common frequency. The coil acting as an inductor L forms an LC resonance tank. The charger uses a Class-E amplifier topology to produce the alternating current in the primary coil around the resonant frequency. Below are the charger 210 features;

Charges IPG 102 wirelessly

Charges up to a maximum depth of 30 mm

Integrated alignment sensor helps align the charger with IPG 102 for higher power transfer efficiency Alignment sensor gives an audible and visual feedback to the user Compact and Portable A protected type of cylindrical Li ion battery is used as the charger 210 battery. A Class-E of the topologies of the power amplifiers has been the most preferred type of amplifier for induction chargers, especially for implantable electronic medical devices. It's relatively high theoretical efficiency made it the most favorable choice for devices where high efficiency power transfer is necessary. A 0.1 ohm high wattage resistor is used in series to sense the current through this circuit.

The primary coil L1 is made by 60 turns of Litz wire type 100/44—100 strands of 44 AWG each. The Litz wire solves the problem of skin effect and keeps its impedance low at high frequencies. Inductance of this coil was initially set at 181 uH, but backing it with a Ferrite plate increases the inductance to 229.7 uH. The attached ferrite plate focuses the produced magnetic field towards the direction of the implant. Such a setup helps the secondary coil receive more magnetic fields and aids it to induce higher power.

When the switch is ON, the resonance is at frequency $$f = \frac{1}{2\pi\sqrt{L1C2}}$$

When the switch is OFF, it shifts to $$f = \frac{1}{2\pi\sqrt{L1\frac{C1C2}{C1+C2}}}$$

In a continuous operation the resonance frequency will be in the range $$\frac{1}{2\pi\sqrt{L1C2}} < f < \frac{1}{2\pi\sqrt{L1\frac{C1C2}{C1+C2}}}$$

To make the ON and OFF resonance frequencies closer, a relatively larger value of C1 can be chosen by a simple criteria as follows
C1=nC2; a value of n=4 was used in the example above; in most cases 3<n<10.

The voltages in these Class-E amplifiers typically go up to the order of 300 VAC. Capacitors selected must be able to withstand these high voltages, sustain high currents and still maintain low Effective Series Resistance (ESR). Higher ESRs result in unnecessary power losses in the form of heat. The circuit is connected to the battery through an inductor which acts as a choke. The choke helps to smoothen the supply to the circuit. The N Channel MOSFET acts as a switch in this Class-E power amplifier. A FET with low ON resistance and with high drain current Id is desirable.

In summary, the circuit is able to recharge the IPG 102 battery 108 from 0 to 100% in 2 Hr 45 Min with distance between the coils being 29 mm. The primary coil and the Class-E amplifier draws DC current of 0.866 A to achieve this task. To improve the efficiency of the circuit, a feedback closed loop control is implemented to reduce the losses. The losses are minimum when the MOSFET is switched ON and when the voltage on its drain side is close to zero.

The controller takes the outputs from operational amplifiers, checks if they meet the criteria, then it triggers the driver to switch ON the MOSFET for next cycle. The controller needs to use a delay timer, an OR gate and a 555 timer in monostable configuration to condition the signal for driver. When the device is switched ON, the circuit does not start to function right away as there will be no active feedback loop. The feedback becomes active only if the circuit starts to function. To solve this riddle, an initial external trigger is applied to jump start the system.

Alignment Sensor

The efficiency of the power transfer between the external charger 210 and the internal IPG 102 will be maximum only when they are properly aligned. An alignment sensor is absolutely necessary to ensure a proper alignment. This is a part of the external circuit design. The first design is based on the principle called reflected impedance. When the external is brought closer to the internal, the impedance of the both circuits change. The sensing is based on measuring the reflected impedance and test whether it crosses the threshold. A beeper is used to give an audible feedback to the patient; an LED is used for visual feedback.

When the impedance of the circuit changes, the current passing through it also changes. A high power 0.1 ohm resistor is used in the series of the circuit to monitor the change in current. The voltage drop across the resistor is amplified 40 times and then compared to a fixed threshold value using an operational amplifier voltage comparator. The output was fed to a timer chip which in turn activates the beeper and LED to give feedback to the user.

This circuit was successfully implemented in the lab on the table top version. The circuit was able to sense the alignment up to a distance of 30 mm. The current fluctuation in the circuit depends on more factors than reflected impedance alone and the circuit is sensitive to other parameters of the circuit as well. To reduce the sensitivity related to other parameters, one option is to eliminate interference of all the other factors and improve the functionality of the reflected impedance sensor—which is very challenging to implement within the limited space available for circuitry. Another option is to use a dedicated sensor chip to measure the reflected impedance.

A second design uses sensors designed for proximity detector or metal detectors for alignment sensing. Chips designed to detect metal bodies by the effect of Eddy currents on the HF losses of a coil can be used for this application. The TDE0160 is an example of such a chip.

The external charger is designed to work at 75 to 80 kHz, whereas the proximity sensor was designed for 1 MHz. The sensor circuit is designed to be compatible with the rest of the external and is fine tuned to detect the internal IPG 102 from a distance of 30 mm.

Programmer

The Clinician Programmer is an application that is installed on a tablet 204. It is used by the clinician to set the stimulation parameters on the trial generator 107 or IPG 102 during trial and permanent implantation in the operating room. The clinician programmer is capable of saving multiple settings for multiple patients and can be used to adjust the stimulation parameters outside of the operations room. It is capable of changing the stimulation parameters though the RF wireless dongle 200 when the trial generator 107 or IPG 102 in the patient is within the RF range. In addition, it is also capable of setting or changing the stimulation parameters on the trial generator 107 and/or the IPG 102 through the internet when both the tablet 204 and the Patient Programmers on a smartphone/mobile device 202 both have access to the internet.

The Patient Programmer is an application that is installed on a smartphone/mobile device 202. It is used by the patient to set the stimulation parameters on the trial generator 107 or IPG 102 after trial and permanent implantation outside the operating room. The clinician programmer is capable of saving multiple settings for multiple patients and can be transferred to the Patient Programmer wirelessly when the Clinician Programmer tablet 204 and the Patient Programmer smartphone/mobile device 202 are within wireless range such as Bluetooth from each other. In the scenario where the Clinician Programmer tablet 204 and the Patient Programmer smartphone/mobile device 202 are out of wireless range from each other, the data can be transferred through the internet where both devices 202, 204 have wireless access such as Wi-Fi. The Patient Programmer is capable of changing the stimulation parameters on the trial generator 107 or IPG 102 though the RF wireless dongle 200 when the trial generator 107 or IPG in the patient is within the RF range. However, the Patient Programmer has limitations to changing the stimulation parameters.

Tuohy Needle

Figure 15:
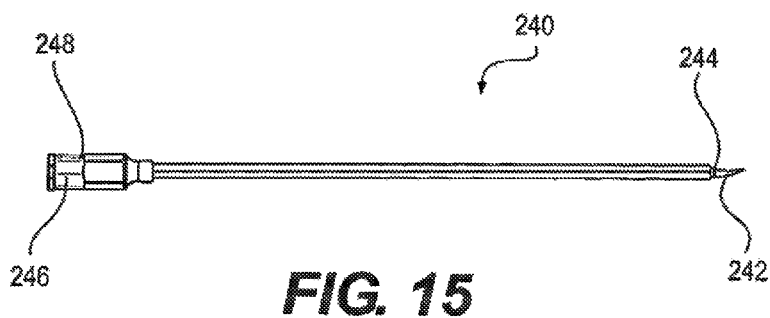
FIG. 15 depicts a Tuohy needle, according to an embodiment.

The tuohy needle 240, as depicted in FIG. 15, is used in conjunction with a saline-loaded syringe for loss-of-resistance needle placement, and percutaneous stimulation leads 140, for lead 140 placement into the spinal canal. The tuohy epidural needle 240 is inserted slowly into the spinal canal using a loss-of-resistance technique to gauge needle 240 depth. Once inserted to the appropriate depth, the percutaneous stimulation lead 140 is passed through the needle 240 and into the spinal canal.

The epidural needle 240 is a non-coring 14G stainless steel spinal needle 240 and will be available in lengths of 5" (127 mm) and 6" (152.4). The distal tip 242 of the needle 240 has a slight curve to direct the stimulation lead 140 into the spinal canal. The proximal end 246 is a standard Leur-Lock connection 248.

Stylet

Figure 16:
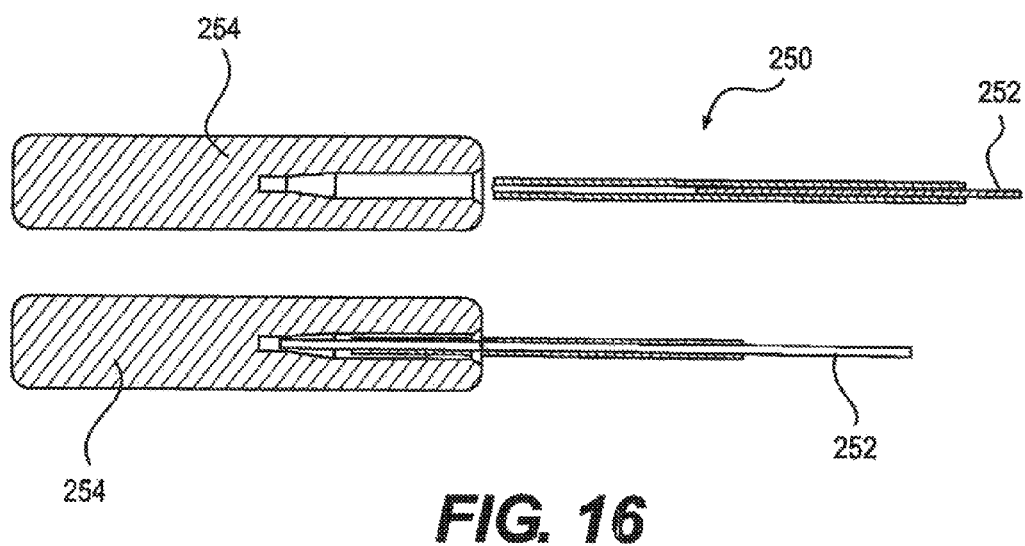
FIG. 16 depicts a stylet, according to an embodiment.

The stylet 250, as depicted in FIG. 16, is used to drive the tip of a percutaneous stimulation lead 140 to the desired stimulation zone by adding rigidity and steerability. The stylet 250 wire 252 passes through the center lumen 142 of the percutaneous lead 140 and stops at the blocking plug at the distal tip of the lead 140. The tip of the stylet 250 comes with both straight and curved tips. A small handle 254 is used at the proximal end of the stylet 250 to rotate the stylet 250 within the center lumen 142 to assist with driving. This handle 254 can be removed and reattached allowing anchors 170 to pass over the lead 140 while the stylet 250 is still in place. The stylet 250 wire 252 is a PTFE coated stainless steel wire and the handle 254 is plastic.

Passing Elevator

Figure 17:
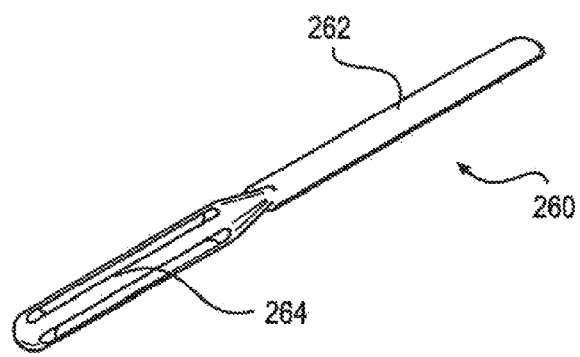
FIG. 17 depicts a passing elevator, according to an embodiment.

The passing elevator 260, as depicted in FIG. 17, is used prior to paddle lead 141 placement to clear out tissue in the spinal canal and help the surgeon size the lead to the anatomy. The passing elevator 260 provides a flexible paddle-shaped tip 262 to clear the spinal canal of obstructions. The flexible tip is attached to a surgical handle 264.

The passing elevator 260 is a one-piece disposable plastic instrument made of a flexible high strength material with high lubricity. The flexibility allows the instrument to easily conform to the angle of the spinal canal and the lubricity allows the instrument to easily pass through tissue.

Tunneling Tool

Figure 18:
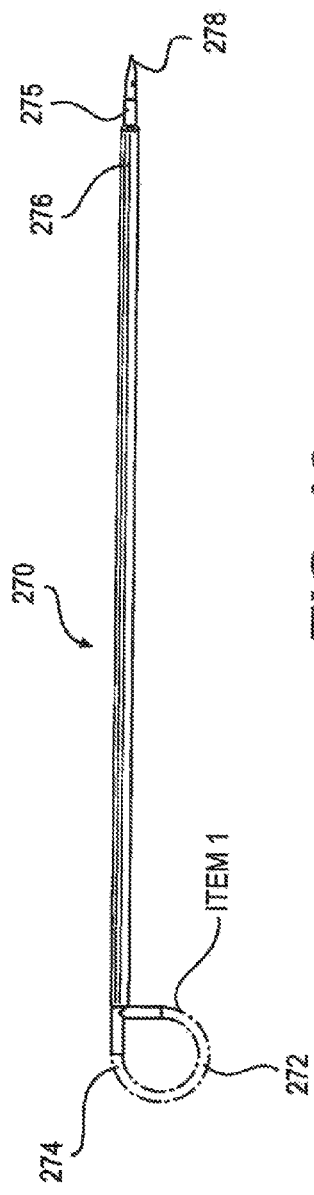
FIG. 18 depicts a tunneling tool, according to an embodiment.

The tunneling tool 270, as depicted in FIG. 18, is used to provide a subcutaneous canal to pass stimulation leads 140 from the entrance point into the spinal canal to the IPG implantation site. The tunneling tool 270 is a long skewer-shaped tool with a ringlet handle 272 at the proximal end 274. The tool 270 is covered by a plastic sheath 276 with a tapered tip 278 which allows the tool 270 to easily pass through tissue. Once the IPG 102 implantation zone is bridge to the lead 140 entrance point into the spinal canal, the inner core 275 is removed, leaving the sheath 276 behind. The leads 140 can then be passed through the sheath 276 to the IPG 102 implantation site. The tunneling tool 270 is often bent to assist in steering through the tissue.

The tunneling tool 270 is made of a 304 stainless steel core with a fluorinated ethylene propylene (FEP) sheath 276. The 304 stainless steel is used for its strength and ductility during bending, and the sheath 276 is used for its strength and lubricity.

Torque Wrench

Figure 19:
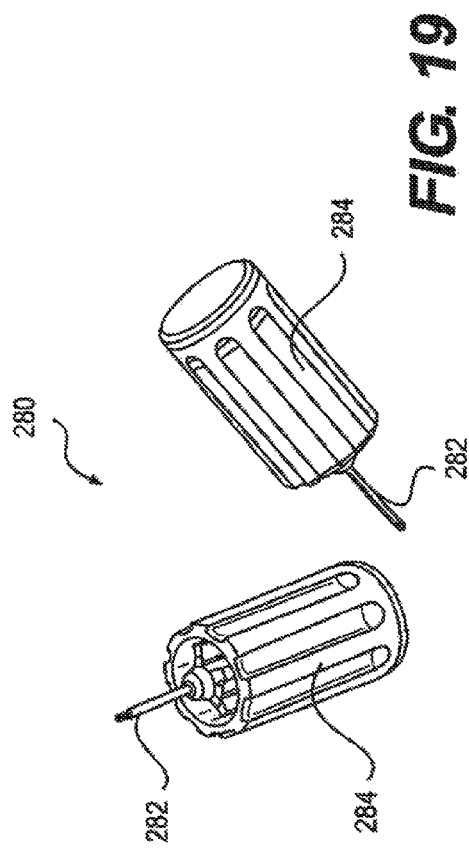
FIG. 19 depicts a torque wrench, according to an embodiment.

The torque wrench 280, as depicted in FIG. 19, is used in conjunction with the IPG 102, lead extension 150 and lead splitter 160 to tighten the internal set screw 119, which provides a radial force against the fixation contact of the stimulation leads 140, 141, preventing the leads 140, 141 from detaching. The torque wrench 280 is also used to lock and unlock the anchor 170. The torque wrench 280 is a small, disposable, medical instrument that is used in every SCS 100 case. The torque wrench 280 provides audible and tactile feedback to the surgeon that the lead 140, 141 is secured to the IPG 102, extension 150, or splitter 160, or that the anchor 170 is in the locked or unlocked position.

The torque wrench 280 is a 0.9 mm stainless steel hex shaft 282 assembled with a plastic body 284. The wrench's 280 torque rating is bi-directional, primarily to provide feedback that the anchor 170 is either locked or unlocked. The torque rating allows firm fixation of the set screws 119, 152 against the stimulation leads 140, 141 without over-tightening.

Trial Patch

The trial patch is used in conjunction with the trialing pulse generator 107 to provide a clean, ergonomic protective cover of the stimulation lead 140, 141 entrance point in the spinal canal. The patch is also intended to cover and contain the trial generator 107. The patch is a large, adhesive bandage that is applied to the patient post-operatively during the trialing stage. The patch completely covers the leads 140, 141 and generator 107, and fixates to the patient with anti-microbial adhesive.

The patch is a watertight, 150 mm×250 mm anti-microbial adhesive patch. The watertight patch allows patients to shower during the trialing period, and the anti-microbial adhesive decreases the risk of infection. The patch will be made of polyethylene, silicone, urethane, acrylate, and rayon.

Magnetic Switch

The magnetic switch is a magnet the size of a coin that, when placed near the IPG 102, can switch it on or off. The direction the magnet is facing the IPG 102 determines if the magnetic switch is switching the IPG 102 on or off.

The invention claimed is:

1. A spinal cord stimulation device comprising:
   an implantable pulse generator;
   a plurality of implantable stimulation electrodes;
   the implantable pulse generator comprising:
      an application specific integrated circuit and a microcontroller, the microcontroller in communication with the application specific integrated circuit, wherein the application specific integrated circuit is configured to receive data from the microcontroller to produce a stimulation pulse train and a high speed burst pulse train, and
      wherein the application specific integrated circuit is configured to combine the stimulation pulse train with the high speed burst pulse train to produce a bursted bi-phasic pulse train that is configured to be received by the plurality of stimulation electrodes.

2. The spinal cord stimulation device of claim 1, further comprising a wireless dongle in communication with the microcontroller.

3. The spinal cord stimulation device of claim 1, wherein the bursted bi-phasic pulse train has a frequency at or below 1200 Hz.

4. The spinal cord stimulation device of claim 1, further comprising a rechargeable battery comprised of an implantable grade lithium ion battery having zero-volt technology wherein the battery is configured to be inductively charged via an external charger.

5. The spinal cord stimulation device of claim 1, wherein the plurality of implantable stimulation electrodes are grouped in stimulation sets, each stimulation set programmable with different stimulation parameters.

6. The spinal cord stimulation device of claim 1, wherein a pulse burst conditioner outputs the bursted bi-phasic pulse train and a timing generator generates rising and falling edge triggers for each phase of the bursted bi-phasic pulse train.

7. The spinal cord stimulation device of claim 6, wherein the application specific integrated circuit includes an analog section configured to analyze the bursted bi-phasic pulse train and convert the bursted bi-phasic pulse train to an analog signal outputted to one of the plurality of implantable stimulation electrodes.

8. The spinal cord stimulation device of claim 7, wherein the application specific integrated circuit includes a digital section that produces the bursted bi-phasic pulse train.

9. The spinal cord stimulation device of claim 1, wherein a clinician programmer application is provided on a computing device and is configured to transmit operational data to the microcontroller.

10. The spinal cord stimulation device of claim 1, wherein the application specific integrated circuit includes a voltage doubler full wave rectifier converts an induced AC voltage into usable DC voltage.

11. A spinal cord stimulation device comprising:
an implantable pulse generator;
a plurality of implantable stimulation electrodes;
the implantable pulse generator comprising:
    an application specific integrated circuit and a microcontroller, the microcontroller in communication with the application specific integrated circuit, wherein the application specific integrated circuit is configured to receive data from the microcontroller to produce a stimulation pulse train and a high speed burst pulse train, and
    wherein the application specific integrated circuit is configured to combine the stimulation pulse train with the high speed burst pulse train to produce a bursted bi-phasic pulse train that is configured to be received by the plurality of stimulation electrodes,
    wherein the application specific integrated circuit comprises a digital section and an analog section, the digital section configured to receive digital data from the microcontroller to produce the bursted bi-phasic pulse train and the analog section containing circuitry to convert the bursted bi-phasic pulse train into a constant current stimulation signal that is transmitted at least one of the plurality of implantable stimulation electrodes.

12. The spinal cord stimulation device of claim 11, further comprising a wireless dongle in communication with the microcontroller.

13. The spinal cord stimulation device of claim 11, wherein the bursted bi-phasic pulse train has a frequency at or below 1200 Hz.

14. The spinal cord stimulation device of claim 11, further comprising a rechargeable battery comprised of an implantable grade lithium ion battery having zero-volt technology wherein the battery is configured to be inductively charged via an external charger.

15. The spinal cord stimulation device of claim 11, wherein the plurality of implantable stimulation electrodes are grouped in stimulation sets, each stimulation set programmable with different stimulation parameters.

16. The spinal cord stimulation device of claim 11, wherein a pulse burst conditioner outputs the bursted bi-phasic pulse train and a timing generator generates rising and falling edge triggers for each phase of the bursted bi-phasic pulse train.

17. The spinal cord stimulation device of claim 16, wherein the analog section is configured to analyze the bursted bi-phasic pulse train and convert the bursted bi-phasic pulse train to an analog signal outputted to one of the plurality of implantable stimulation electrodes.

18. The spinal cord stimulation device of claim 17, wherein the digital section comprises timing generators, arbitration control, pulse Burst Conditioner, and electrode Logic.

19. The spinal cord stimulation device of claim 11, wherein a clinician programmer application is provided on a computing device and is configured to transmit operational data to the microcontroller.

20. The spinal cord stimulation device of claim 11, wherein the application specific integrated circuit includes a voltage doubler full wave rectifier converts an induced AC voltage into usable DC voltage.

* * * * *